United States Patent
Morin et al.

(10) Patent No.: US 10,670,590 B2
(45) Date of Patent: *Jun. 2, 2020

(54) TARGET DETECTION WITH NANOPORE

(71) Applicant: Ontera Inc., Santa Cruz, CA (US)

(72) Inventors: Trevor J. Morin, Santa Cruz, CA (US); William B. Dunbar, Santa Cruz, CA (US); Daniel Alexander Heller, Santa Cruz, CA (US)

(73) Assignee: Ontera Inc., Santa Cruz, CA (US)

( * ) Notice: Subject to any disclaimer, the term of this patent is extended or adjusted under 35 U.S.C. 154(b) by 493 days.

This patent is subject to a terminal disclaimer.

(21) Appl. No.: 14/991,851

(22) Filed: Jan. 8, 2016

(65) Prior Publication Data

US 2016/0245802 A1 Aug. 25, 2016

Related U.S. Application Data

(63) Continuation-in-part of application No. PCT/US2014/046397, filed on Jul. 11, 2014, which is
(Continued)

(51) Int. Cl.
| | |
|---|---|
| *G01N 33/536* | (2006.01) |
| *G01N 33/543* | (2006.01) |
| *C12Q 1/6825* | (2018.01) |
| *G01N 33/68* | (2006.01) |
| *C12Q 1/6804* | (2018.01) |
| *G01N 33/537* | (2006.01) |
| *C12Q 1/6869* | (2018.01) |

(Continued)

(52) U.S. Cl.
CPC ..... *G01N 33/54306* (2013.01); *C12Q 1/6804* (2013.01); *C12Q 1/6825* (2013.01); *C12Q 1/6869* (2013.01); *G01N 33/537* (2013.01); *G01N 33/54366* (2013.01); *G01N 33/6872* (2013.01); *B82Y 15/00* (2013.01); *G01N 33/48721* (2013.01)

(58) Field of Classification Search
CPC .. C12Q 1/6804; C12Q 1/6825; C12Q 1/6869; G01N 33/537; G01N 33/6872; G01N 33/48721; B82Y 15/00
See application file for complete search history.

(56) References Cited

U.S. PATENT DOCUMENTS

| | | |
|---|---|---|
| 5,965,361 A | 10/1999 | Kigawa et al. |
| 7,947,485 B2 | 5/2011 | Wu et al. |

(Continued)

FOREIGN PATENT DOCUMENTS

| | | |
|---|---|---|
| CN | 103364445 A | 10/2013 |
| CN | 104109633 A | 10/2014 |
| WO | WO-03/044482 A2 | 5/2003 |
| WO | WO 2013012881 A2 | 1/2013 |
| WO | WO 2013/123450 | 8/2013 |
| WO | WO 2018/093976 A1 | 5/2018 |

OTHER PUBLICATIONS

Communication pursuant to Article 94(3) EPC for European Patent Application No. EP 14733761.2, dated Aug. 22, 2017, 3 Pages.
(Continued)

*Primary Examiner* — Christopher L Chin
(74) *Attorney, Agent, or Firm* — Fenwick & West LLP

(57) ABSTRACT

Provided are methods and compositions for detecting a target molecule or particle suspected to be present in a sample using a polymer scaffold, a fusion molecule, and a pore.

17 Claims, 15 Drawing Sheets

Related U.S. Application Data a continuation of application No. PCT/US2014/036861, filed on May 5, 2014, application No. 14/991,851, which is a continuation-in-part of application No. 14/270,283, filed on May 5, 2014, now abandoned.

(60) Provisional application No. 62/101,262, filed on Jan. 8, 2015, provisional application No. 61/820,083, filed on May 6, 2013.

(51) Int. Cl.
*G01N 33/487* (2006.01)
*B82Y 15/00* (2011.01)

(56) References Cited

U.S. PATENT DOCUMENTS

| | | | |
|---|---|---|---|
| 8,557,529 B2 | 10/2013 | Polonsky et al. | |
| 9,983,191 B2 | 5/2018 | Morin | |
| 10,048,245 B2 | 8/2018 | Morin et al. | |
| 2004/0197793 A1 | 10/2004 | Hassibi et al. | |
| 2004/0224336 A1 | 11/2004 | Wagner | |
| 2005/0026202 A1 | 2/2005 | Edman et al. | |
| 2008/0050752 A1 | 2/2008 | Sun et al. | |
| 2009/0050492 A1 | 2/2009 | Alocilja et al. | |
| 2012/0276530 A1 | 11/2012 | Meller et al. | |
| 2013/0233709 A1 | 9/2013 | Dunbar et al. | |
| 2014/0318962 A1 | 10/2014 | Luan et al. | |
| 2014/0329225 A1* | 11/2014 | Morin | G01N 33/54306 435/5 |
| 2014/0378331 A1* | 12/2014 | Morin | G01N 33/48721 506/9 |
| 2015/0337366 A1 | 11/2015 | Davis et al. | |
| 2016/0200773 A1* | 7/2016 | Morin | C12Q 1/6818 506/9 |
| 2016/0245802 A1* | 8/2016 | Morin | G01N 33/54366 |
| 2016/0258939 A1 | 9/2016 | Morin et al. | |
| 2017/0074855 A1* | 3/2017 | Morin | G01N 33/54366 |
| 2017/0349940 A1* | 12/2017 | Morin | C12Q 1/6825 |
| 2018/0023114 A1* | 1/2018 | Morin | C12Q 1/37 |
| 2018/0023115 A1 | 1/2018 | Morin et al. | |
| 2018/0155768 A1 | 6/2018 | Cohen et al. | |
| 2019/0055592 A1 | 2/2019 | Morin et al. | |

OTHER PUBLICATIONS

Communication pursuant to Article 94(3) EPC for European Patent Application No. EP 14747765.7, dated Aug. 23, 2017, 3 Pages.
Office Action for U.S. Appl. No. 15/160,697, dated Oct. 23, 2017, 15 Pages.
Haque, et al., "Solid-State and Biological Nanopore for Real-Time Sensing of Single Chemical and Sequencing of DNA," Nano Today, 2013, 8, pp. 56-74.
Howorka, et al., "Nanopore Analytics: Sensing of Single Molecules," Chem. Soc. Rev., 2009, 38, pp. 2360-2384.
Miles, et al., "Single Molecule Sensing With Solid-State Nanopores: Novel Materials, Methods, and Applications," Chem Soc Rev, 2013, 42(15), pp. 1-15.
Reiner, et al., "Disease Detection and Management Via Single Nanopore-Based Sensors," Chemical Reviews, 2012, 112, pp. 6431-6451.
Singer, et al., "Nanopore Based Sequence Specific Detection of Duplex DNA for Genomic Profiling," Nano Lett., 2010, 10, pp. 738-742.
Office Action for U.S. Appl. No. 15/160,697, dated Jan. 11, 2017, 32 Pages.
Communication pursuant to Article 94(3) EPC for European Patent Application No. EP 14733761.2, dated Jan. 17, 2017, 3 Pages.
Bezrukov S. M. et al: "Counting Polymers Moving Through a Single Ion Channel", Nature, Jul. 28, 1994, pp. 279-281, vol. 370, Nature Publishing Group, United Kingdom.
Kasianowicz J. et al: "Simultaneous Multianalyte Detection with a Nanometer-Scale Pore", Analytical Chemistry, May 15, 2001, pp. 2268-2272, vol. 73(10).
Niemeyer C M: "The developments of semisynthetic DNA-protein conjugates", Trends in Biotechnology, Sep. 2002, pp. 395-401, vol. 20(9), Elsevier Publications, Cambridge, GB.
Wanunu M. et al: "DNA Profiling Using Solid-State Nanopores: Detection of DNA-Binding Molecules", Nano Letters, Oct. 14, 2009, pp. 3498-3502, vol. 9 (10).
Winters-Hilt S. "Nanopore Detector based analysis of single-molecule conformational kinetics and binding interactions", Sep. 26, 2006, pp. 1-27, vol. 7(2), BMC Bioinformatics, Biomed Central, London, GB.
International Search Report and Written Opinion for International Application No. PCT/US2014/036861, dated Sep. 18, 2014, 12 pages.
PCT Written Opinion of the International Preliminary Examining Authority for PCT/US2014/036861, dated Apr. 15, 2015, 7 Pages.
PCT International Search Report and Written Opinion for PCT/US2014/046397, dated Feb. 2, 2015, 11 Pages.
International Preliminary Report on Patentability for PCT/US2014/036861, dated Sep. 2, 2015, 8 Pages.
Office Action for U.S. Appl. No. 14/270,283, dated Dec. 11, 2015, 6 Pages.
Kowalczyk, S.W. et al., "Detection of Local Protein Structures along DNA Using Solid-State Nanopores," Nano Letters, 2010, vol. 10, pp. 324-328.

\* cited by examiner

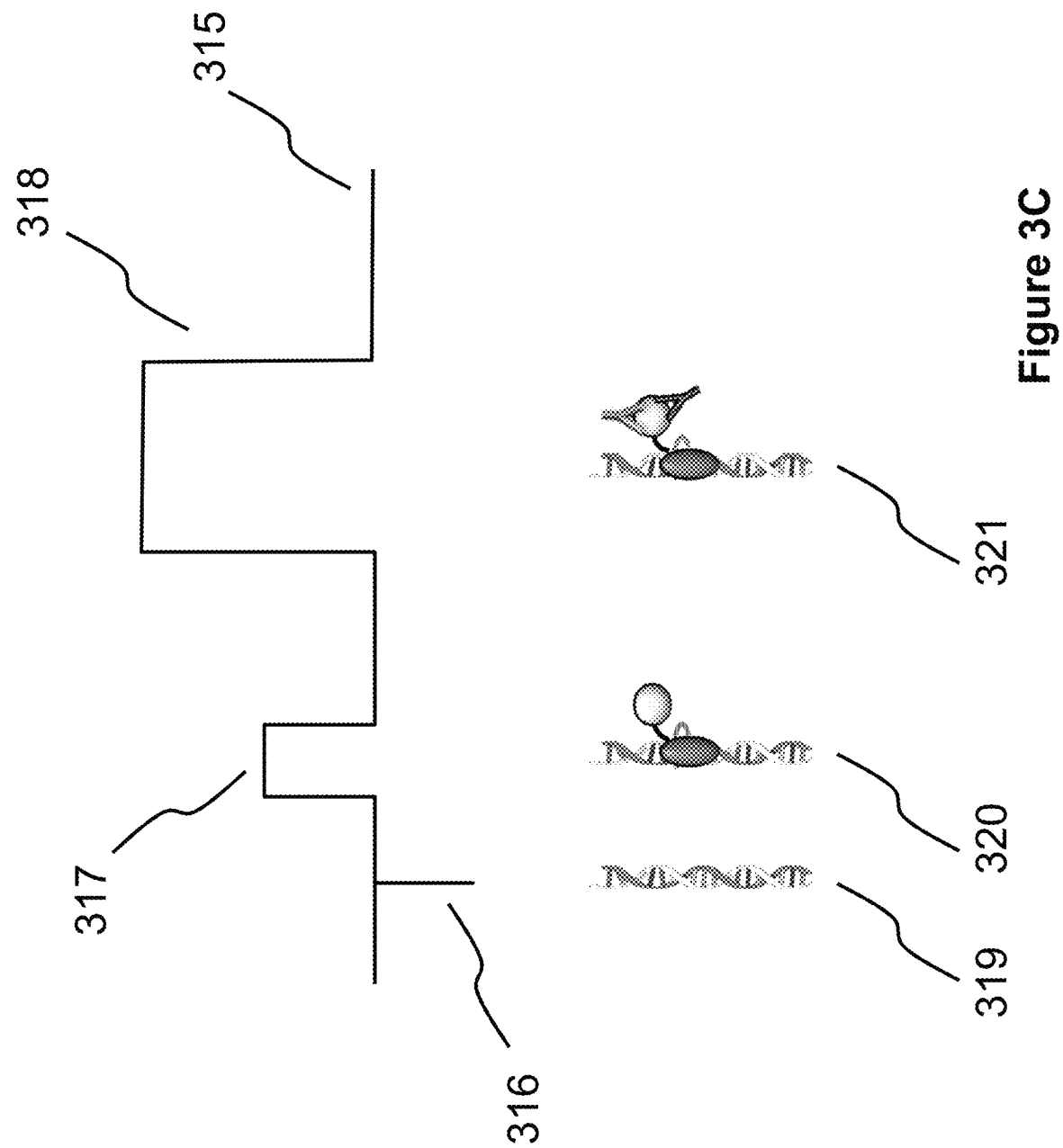

TARGET DETECTION WITH NANOPORE

RELATED APPLICATIONS

The present application claims priority to U.S. Provisional Application 62/101,262, filed on Jan. 8, 2015. The present application is also a continuation-in-part of PCT Application PCT/US2014/046397, filed Jul. 11, 2014. PCT Application PCT/US2014/046397 claimed priority to PCT Application PCT/US2014/036861, filed May 5, 2014. The present application is also a continuation-in-part of U.S. application Ser. No. 14/270,283, filed May 5, 2014. U.S. application Ser. No. 14/270,283 claimed priority to U.S. Provisional Application 61/820,083, filed May 6, 2013. All the foregoing applications are incorporated herein by reference in their entireties for any and all purposes.

BACKGROUND

Detection of nano-scale and micro-scale particles, such as circulating tumor cells, bacteria and viruses, has immense clinical utility. Currently available methods include immunohistochemistry and nucleic acid-based detection, and cell proliferation is typically required before a sensitive detection can be carried out.

Molecular detection and quantitation are also important, and can be carried out with various methods depending on the type of the molecule. For instance, a nucleotide sequence can be detected by virtue of its sequence complementarity to a probe or primer, through hybridization and/or amplification, or in fewer occasions, with a protein that recognizes the sequence. A protein, on the other hand, is commonly detected with an antibody that specifically recognizes and binds the protein. An enzyme-linked immuno sorbent assay (ELISA), in this respect, is highly commercialized and commonly used.

Methods also exist for detecting or quantitating various other large or small molecules, such as carbohydrates, chemical compounds, ions, and elements.

Methods and systems for highly sensitive detection of molecules as well as particles, such as tumor cells and pathogenic organisms, have broad applications, in particular clinically, for pathogen detection and disease diagnosis, for instance. Additionally, such detection may: allow for the personalization of medical treatments and health programs; facilitate the search for effective pharmaceutical drug compounds and biotherapeutics; and enable clinicians to identify abnormal hormones, ions, proteins, or other molecules produced by a patient's body and/or identify the presence of poisons, illegal drugs, or other harmful chemicals ingested or injected into a patient.

Currently available techniques for the detection of molecules and particles are generally expensive, labor-intensive, skill-intensive, and/or time-intensive. A need exists for improved detection techniques, which produce accurate results quickly, cheaply, and easily.

SUMMARY

Various aspects disclosed herein may fulfill one or more of the above-mentioned needs. The systems and methods described herein each have several aspects, no single one of which is solely responsible for its desirable attributes. Without limiting the scope of this disclosure as expressed by the claims that follow, the more prominent features will now be discussed briefly. After considering this discussion, and particularly after reading the section entitled "Detailed Description," one will understand how the sample features described herein provide for improved systems and methods.

In an embodiment, the present disclosure provides a method for detecting the presence or absence of a target molecule suspected to be present in a sample, comprising: contacting the sample with a polymer scaffold bound to a fusion molecule, wherein the fusion molecule comprises a target molecule binding domain configured to selectively bind to the target molecule, and wherein the fusion molecule is non-specifically bound to the polymer scaffold; loading the polymer scaffold into a device comprising a pore that separates an interior space of the device into two volumes, and configuring the device to pass the polymer scaffold through the pore from one volume to the other volume, wherein the device comprises a sensor configured to identify objects passing through the pore; and determining, with the sensor, whether the target molecule binding domain is bound to a target molecule upon translocation through the pore, thereby detecting the presence or absence of the target molecule in the sample.

In some embodiments, the polymer scaffold comprises a polynucleotide or a polypeptide. In some embodiments, the polynucleotide comprises a deoxyribonucleic acid (DNA), a ribonucleic acid (RNA), or a peptide nucleic acid (PNA). In some embodiments, the target molecule is selected from the group consisting of: a protein, a peptide, a polynucleotide, a chemical compound, an ion, and an element. In some embodiments, the determining step is performed $1\times10^3$, $1\times10^4$, $1\times10^5$, $1\times10^6$ or more times for each sample.

In some embodiments, the polymer scaffold is covalently linked to said fusion molecule. In some embodiments, the polymer scaffold is cross-linked to said fusion molecule.

In some embodiments, the fusion molecule comprises a polymer scaffold binding domain. In some embodiments, the polymer scaffold comprises a polynucleotide. In some embodiments, the polymer scaffold binding domain binds to the backbone of the polynucleotide. In some embodiments, the polymer scaffold binding domain binds a chemically modified region of said polymer scaffold. In some embodiments, the chemical modification is selected from the group consisting of: acetylation, methylation, summolation, glycosylation, phosphorylation, biotinylation, and oxidation. In some embodiments, the polymer scaffold binding domain recognizes and binds a sequence of no more than 6, 5, 4, 3, or 2 nucleotides. In some embodiments, the polymer scaffold binding domain recognizes and binds a sequence of the polymer scaffold that is present in an average probability frequency of at least once every 20,000, 10,000, 5,000, 2,000, 1,000, 500, 200, or 100 base pairs. In some embodiments, the polymer scaffold binding domain recognizes and binds a sequence of the polymer scaffold that is present in naturally occurring frequency of at least once every 20,000, 10,000, 5,000, 2,000, 1,000, 500, 200, or 100 base pairs. In some embodiments, the polymer scaffold comprises a non-engineered binding domain recognized by the polymer scaffold binding domain of the fusion molecule.

In some embodiments, step (a) is performed prior to step (b). In other embodiments, step (b) is performed prior to step (a).

In some embodiments, the method of detecting the presence or absence of a target molecule suspected to be present in a sample further comprises applying a condition suspected to alter the binding between the target molecule or particle and the target molecule binding domain, and repeating the step of determining the binding state of the fusion molecule. In some embodiments, the condition is selected from the group consisting of: removing the target molecule or particle from the sample, adding an agent that competitively binds to the target molecule or target molecule binding domain, and changing the pH, salt, or temperature.

In some embodiments, the polymer scaffold comprises a chemical modification for binding to the polymer scaffold. In some embodiments, the chemical modification is selected from the group consisting of: acetylation, methylation, summolation, glycosylation, phosphorylation, biotinylaton, and oxidation.

In some embodiments, the method of detecting the presence or absence of a target molecule suspected to be present in a sample further comprises contacting the sample with a detectable label capable of binding to the target molecule, or to the target molecule/fusion molecule complex.

In some embodiments, the polymer scaffold comprises at least two binding motifs. In some embodiments, the polymer comprises at least two different binding motifs; the sample is in contact with at least two fusion molecules each comprising a different binding domain capable of binding to a different one of the at least two different binding motifs and a different ligand capable of binding to a different target molecule or particle; and the sensor is configured to identify whether the fusion molecule bound to each binding motif is bound to a target molecule or particle. In some embodiments, the sensor comprises electrodes configured to apply a voltage differential between the two volumes and measure current flow through the pore.

In some embodiments, the device used in the method for detecting the presence or absence of a target molecule suspected to be present in a sample comprises an upper chamber, a middle chamber and a lower chamber, wherein the upper chamber is in communication with the middle chamber through a first pore, and the middle chamber is in communication with the lower chamber through a second pore; wherein the first pore and second pore are configured to simultaneously translocate the same polymer scaffold; and wherein each of the chambers comprises an electrode for connecting to a power supply. In some embodiments, the method for detecting the presence or absence of a target molecule suspected to be present in a sample further comprises applying independent voltages across each pore with a common ground in the middle chamber to capture the polymer first into both pores, and subsequently using voltage control logic to move and control the polymer scaffold in any direction after the binding motif passes through the pore, to detect and re-detect whether the fusion molecule bound to each binding motif is bound to a target molecule or particle.

Also provided herein is a kit, package or mixture for detecting the presence of a target molecule or particle, the kit comprising: a fusion molecule comprising a target molecule binding domain capable of binding to the target molecule, and further comprising a polymer scaffold binding domain, wherein said polymer scaffold binding domain binds non-specifically to said polymer scaffold; and a polymer scaffold comprising at least one binding motif to which the binding domain is capable of binding.

In some embodiments, the kit, package or mixture further comprises a device comprising a pore that separates an interior space of the device into two volumes, wherein the device is configured to allow the polymer to pass through the pore from one volume to the other volume, and wherein the device further comprises a sensor adjacent to the pore configured to identify whether the polymer scaffold is (i) bound to the fusion molecule while the fusion molecule is bound to the target molecule, (ii) bound to the fusion molecule while the fusion molecule is not bound to the target molecule or particle, or (iii) not bound to the fusion molecule. In some embodiments, the kit, package or mixture further comprises a sample suspected of containing the target molecule or particle. In some embodiments, of the kit, package or mixture, the sample comprises a detectable label capable of binding to the target molecule, or the target molecule/fusion molecule complex.

BRIEF DESCRIPTION OF THE DRAWINGS

Provided as embodiments of this disclosure are drawings that illustrate by exemplification only, and not limitation, wherein:

FIGS. 3A, 3B, and 3C show representative and idealized current profiles of three example molecules, demonstrating that binding between a target molecule (or particle) and a fusion molecule can be detected when passing through a nanopore, since it has a different current profile, compared to that of the fusion molecule alone or the DNA alone. Specifically, FIG. 3A shows current profiles consistent with higher salt concentrations (>0.4 M KCl, for example at 1M KCl) in the experimental buffer and a positive applied voltage, generating a positive current flow through the pore, and attenuations in the current each time a molecule goes through the pore. By another example, FIG. 3B shows current profiles consistent with lower salt concentrations (<0.4 M KCl, for example at 100 mM KCl) in the experimental buffer and again at a positive applied voltage, with DNA alone enhancing the current while fusion-bound DNA complexes with and without target molecules attenuate the current. By another example, FIG. 3C shows current profiles consistent with lower salt concentrations (<0.4 M KCl, for example at 100 mM KCl) in the experimental buffer and a negative applied voltage. Polarity is reversed compared to the signals in FIG. 3B, as would be the case with reagents in the opposite chamber.

Specifically, FIG. 5A is a diagram of a dual-pore chip and a dual-amplifier electronics configuration for independent voltage control (V1 or V2) and current measurement (I1 or I2) of each pore. Three chambers, A-C, are shown and are volumetrically separated except by common pores.

FIG. 5B is a diagram where electrically, V1 and V2 are principally applied across the resistance of each nanopore by constructing a device that minimizes all access resistances to effectively decouple I1 and I2.

FIG. 5C is a diagram in which competing voltages are used for control, with arrows showing the direction of each voltage force.

FIG. 6A depicts a schematic diagram of the nanopore device. FIG. 6B depicts a representative current trace showing a blockade event resulting from the passage of a double-stranded DNA passing through the pore. The mean current amplitude shift amount ($\Delta I = I_0 - I_B$) and duration $t_D$ are used to quantify the passage event. FIG. 6C depicts a scatter plot showing the mean change in current amount ($\Delta I$) vs. translocation time ($t_D$) for all blockade events recorded over 16 minutes.

(FIG. 10A) maximum conductance in nS (maximum current shift in pA divided by voltage in mV) vs. time duration in seconds, with time duration on a log-scale.

Specifically.

Figure 1:
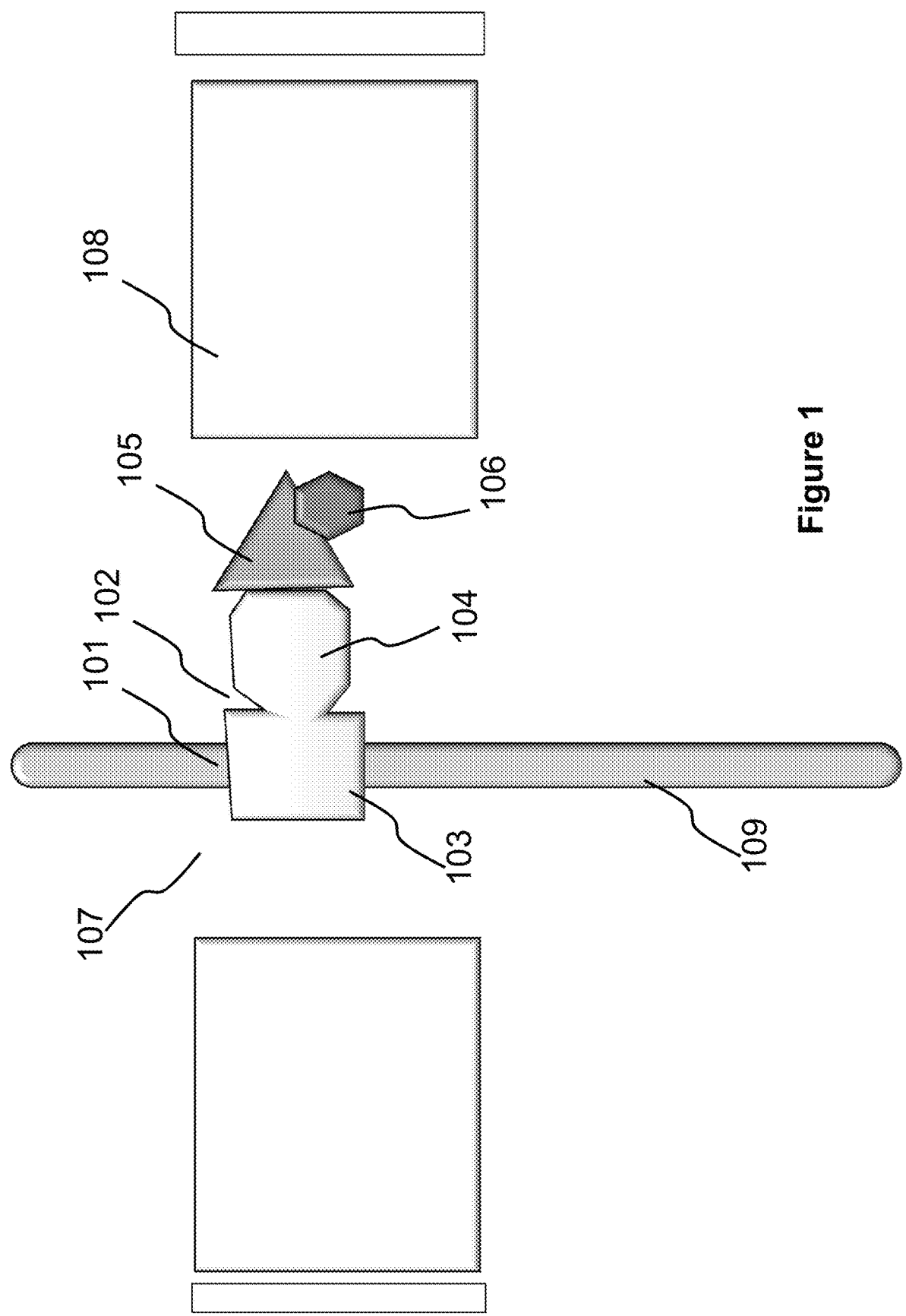
FIG. 1 illustrates the detection of a target molecule or particle with one embodiment of the presently disclosed method.

Some or all of the figures are schematic representations for exemplification; hence, they do not necessarily depict the actual relative sizes or locations of the elements shown. The figures are presented for the purpose of illustrating one or more embodiments with the explicit understanding that they will not be used to limit the scope or the meaning of the claims that follow below.

DETAILED DESCRIPTION

Throughout this application, the text refers to various embodiments of the present devices, compositions, systems, and methods. The various embodiments described are meant to provide a variety of illustrative examples and should not be construed as descriptions of alternative species. Rather, it should be noted that the descriptions of various embodiments provided herein may be of overlapping scope. The embodiments discussed herein are merely illustrative and are not meant to limit the scope of the present invention.

Also throughout this disclosure, various publications, patents and published patent specifications are referenced by an identifying citation. The disclosures of these publications, patents and published patent specifications are hereby incorporated by reference into the present disclosure in their entireties.

As used in the specification and claims, the singular form "a", "an" and "the" include plural references unless the context clearly dictates otherwise. For example, the term "an electrode" includes a plurality of electrodes, including mixtures thereof.

As used herein, the term "comprising" is intended to mean that the systems, devices, and methods include the recited components or steps, but not excluding others. "Consisting essentially of" when used to define systems, devices, and methods, shall mean excluding other components or steps of any essential significance to the combination. "Consisting of" shall mean excluding other components or steps. Embodiments defined by each of these transition terms are within the scope of this invention.

All numerical designations, e.g., distance, size, temperature, time, voltage and concentration, including ranges, are approximations which are varied (+) or (−) by increments of 0.1. It is to be understood, although not always explicitly stated that all numerical designations are preceded by the term "about". It also is to be understood, although not always explicitly stated, that the components described herein are merely exemplary, and that equivalents of such are known in the art.

As used herein, "a device comprising a pore that separates an interior space" shall refer to a device having a pore that comprises an opening within a structure, the structure separating an interior space into more than one volume or chamber.

As used herein, "non-specifically bound" or "non-specific binding" refers to an interaction between a polymer scaffold and a fusion molecule wherein the polymer scaffold binding domain on the fusion molecule can bind to sites commonly present on a polymer scaffold. As an example, for a polynucleotide binding to a protein or other fusion molecule, a non-specific binding interaction may occur due to the recognition and binding of a secondary structure, such as a backbone, minor groove, or major groove, or to a short sequence that is common to the polynucleotide. Non-specific binding may also be to modified aspects of the polymer scaffold other than sequence, such as biotin moieties incorporated into the polymer at one or more non-specific locations. For example, biotin modified dATP can be used in a PCR reaction allowing incorporation of biotin at non-specific locations in that a biotin moiety will be everywhere in the sequence that a biotin-dATP is incorporated. Its realized this provides some specificity, as all dATP sites will be biotinylated. Additionally, biotin-dATP can be mixed with dATP (non-biotin) to truly allow random incorporation of biotinylated-Adenine throughout a DNA molecule. For the purpose of this application, we are considering the former and latter scenarios to allow non-specificity of a molecule that binds to a biotinylated site. Non-specific binding may also be understood in contrast to specific binding, wherein a polymer scaffold binding domain on the fusion molecule binds specifically to sequence at a known site (e.g., an engineered sequence or a known site-specific sequence).

As used herein, the term "recognize" refers to the ability of a binding site or domain to discriminate sequences or structural features to bind with specificity only to a certain binding motif or domain on another molecule or complex. For example, the polymer scaffold binding domain on a fusion molecule can be configured to recognize certain structural features or short sequences on a polymer scaffold.

As used herein, the term "binding domain" or "binding motif" refers to a portion of a molecule that binds to another molecule. The binding can be specific (e.g., specific binding of a biomolecule to a specific sequence of a polynucleotide) or non-specific (e.g., binding to motifs that are common to the molecule (e.g., a common structure or sequence in a polynucleotide). In some embodiments, a binding domain or binding motif present on a polymer scaffold represents the region of binding of a fusion molecule to the scaffold. In some embodiments, the fusion molecules comprises a polymer scaffold binding domain (i.e., binding domain or binding motif) and a target molecule binding domain (i.e., a ligand).

Molecular Detection

The present disclosure provides methods and systems for molecular detection and quantitation. In addition, the methods and systems can also be configured to measure the affinity of a molecule binding with another molecule. Further, such detection, quantitation, and measurement can be carried out in a multiplexed manner, greatly increasing its efficiency.

FIG. 1 provides an illustration of one embodiment of the disclosed methods and systems. More specifically, the system includes a ligand 104 that is capable of binding to a target molecule 105 to be detected or quantitated. The ligand 104 can be part of, or be linked to, a binding moiety (referred to as "binding domain") 103 that is capable of binding to the scaffold at a region denoted as 101 on a polymer scaffold 109. Together, the ligand 104 and the binding domain 103 form a fusion molecule 102. In various embodiments, the ligand 104 binds to the respective targets (e.g., target molecule 105) with high affinity and specificity. The binding domain 103 binds to the scaffold with moderate to high affinity, but are not site specific (i.e., lack specificity) as it will bind anywhere along the scaffold.

Therefore, if all present in a solution, the fusion molecule 102 binds, on one end, to a polymer scaffold (or simply, "polymer") 109 through the recognition and binding between the binding motif 101 and the binding domain 103, and on the other end, to the target molecule 105 by virtue of the interaction between the ligand 104 and the target molecule 105. Such bindings cause the formation of a complex that includes the polymer 109, the fusion molecule 102 and the target molecule 105.

The formed complex can be detected using a that includes a nanopore (or simply, pore) 107, and a sensor. The pore 107 is a nano-scale or micro-scale opening in a structure separating two volumes or reservoirs. The sensor 107 may be positioned within or adjacent to the pore 107 or elsewhere within the two volumes. The sensor is configured to identify objects passing through the pore 107. For example, in some embodiments, the sensor identifies objects passing through the pore 107 by detecting a change in a measurable parameter, wherein the change is indicative of an object passing through the pore 107. This device is referred throughout as a "nanopore device". In some embodiments, the nanopore device 108 includes means, such as electrodes connected to power sources, for moving the polymer 109 from one volume to another through the pore 107. As the polymer 109 can be charged or be modified to contain charges, one example of such means generates a potential or voltage across the pore 107 to facilitate and control the movement of the polymer 109. In a preferred embodiment, the sensor comprises a pair of electrodes, which are configured to both detect the passage of objects, and provide a voltage, across the pore 107. In this embodiment, a voltage-clamp or a patch-clamp is used to simultaneously supply a voltage across the pore and measure the current through the pore.

When a sample that includes the formed complex is loaded in the nanopore device 108, the nanopore device 108 can be configured to pass the polymer 109 through the pore 107. When the binding motif 101 is within the pore or adjacent to the pore 107, the binding status of the motif 101 can be detected by the sensor.

The "binding status" of a binding motif, as used herein, refers to whether the binding motif is bound to a fusion molecule with a corresponding binding domain, and whether the fusion molecule is also bound to a target molecule. Essentially, the binding status can be one of three potential statuses: (i) the binding motif is free and not bound to a fusion molecule (see 305 in FIG. 3A); (ii) the binding motif is bound to a fusion molecule that does not have a target molecule bound (see 306 in FIG. 3A); or (iii) the binding motif is bound to a fusion molecule that is bound to a target molecule (see 307 in FIG. 3A).

Figure 3A:
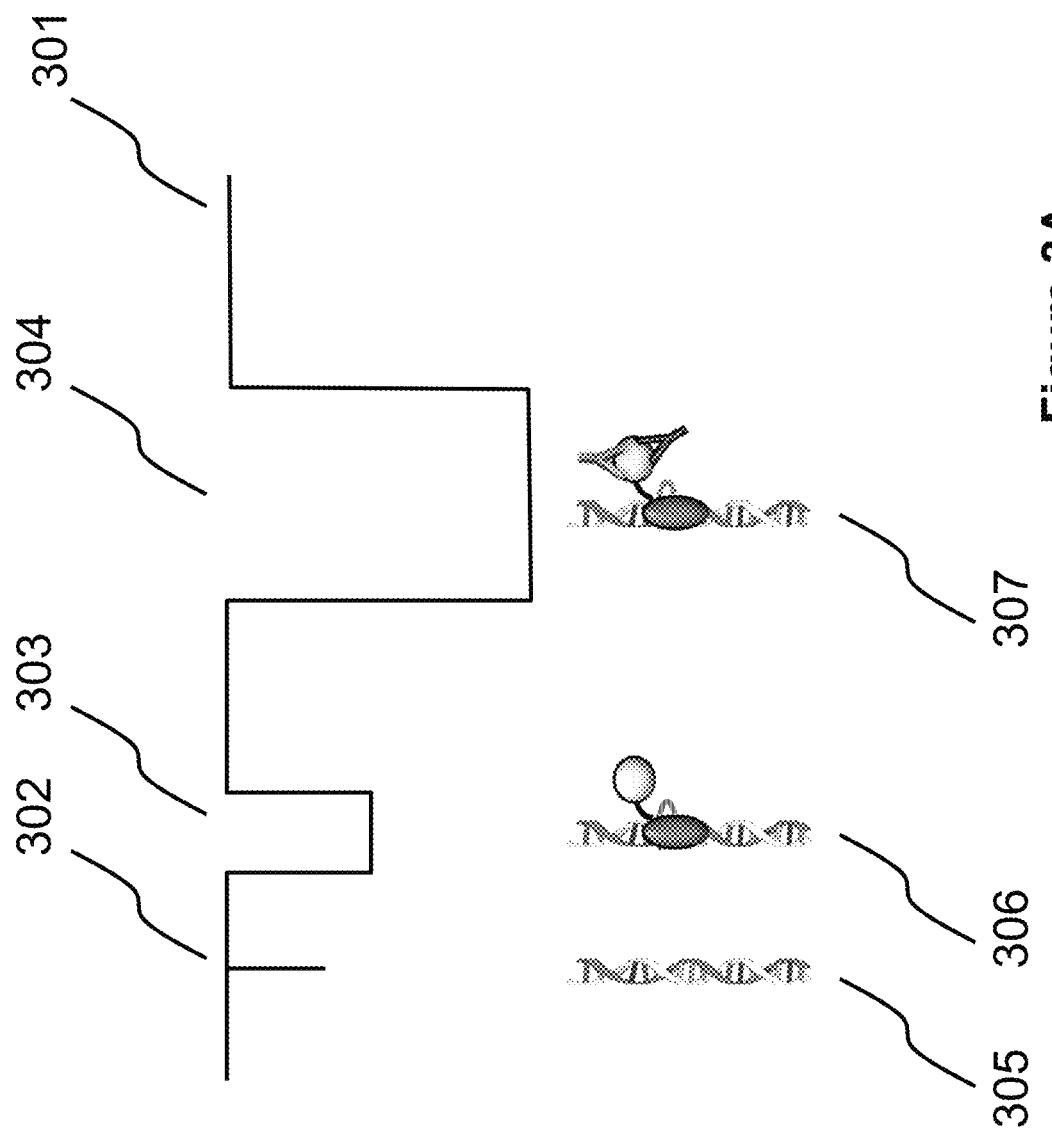
Figure 3B:
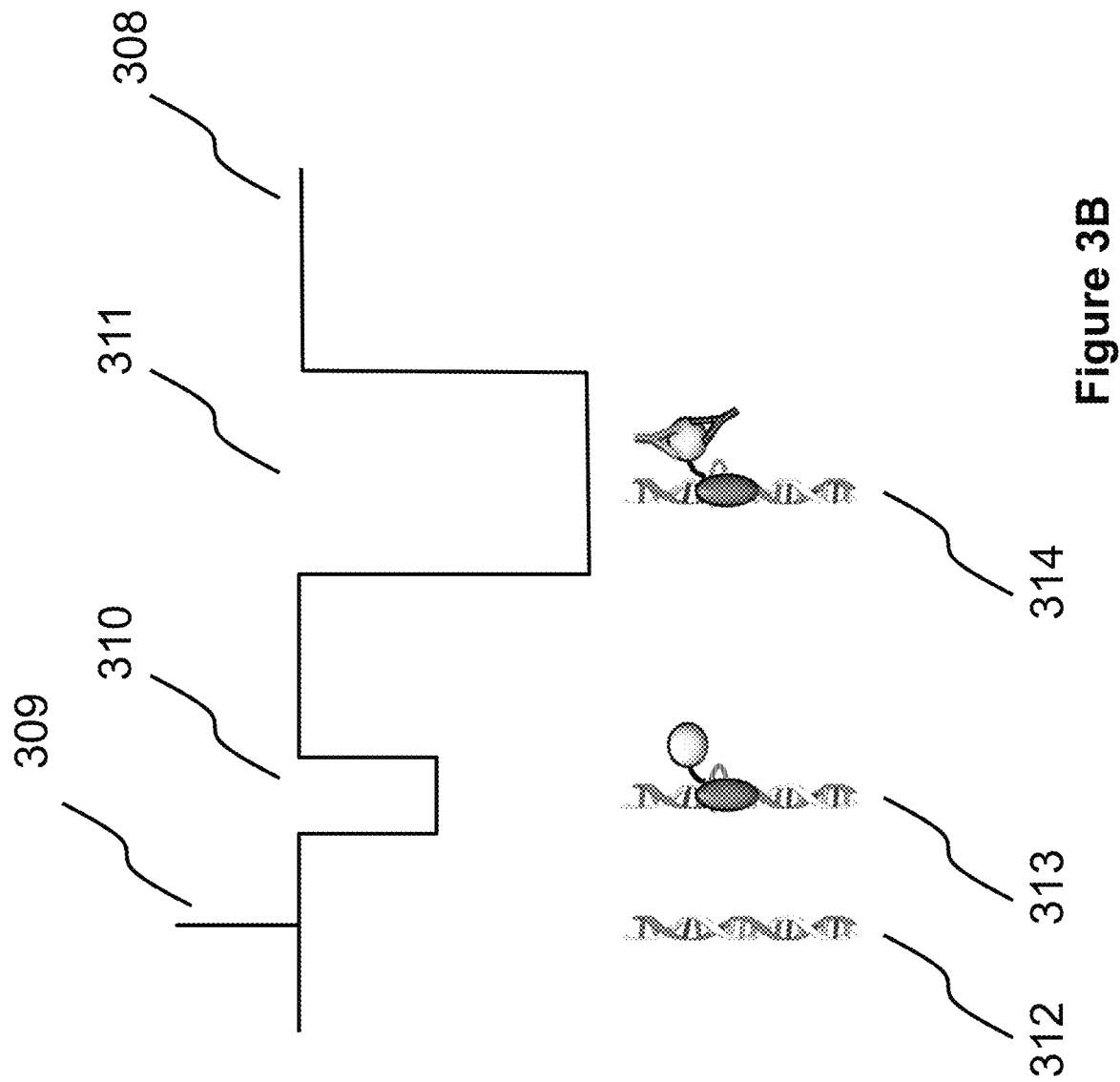

Detection of the binding status of a binding motif can be carried out by various methods. In one aspect, by virtue of the different sizes of the binding motif at each status, when the binding motif passes through the pore, the different sizes result in different electrical current variations through the pore. In one aspect, as shown in FIG. 3A, with a positive voltage applied and KCl concentrations greater than 0.4 M in the experiment buffer, the measured current signals 301, when 305, 306, and 307 pass through the pore, are signals 302, 303, and 304, respectively. All three event types are subjected to current attenuation when KCl concentrations are greater than 0.4 M, causing a reduction in the positive current flow. The three signals 302, 303, and 304 can be differentiated from one another by the amount of the current shift (height) and/or the duration of the current shift (width), or by any other feature in the signal that differentiates the three event types. It may also be that 304 is commonly different than 302 and 303, but that 302 and 303 are not commonly different from each other, in which case, robust detection of the biomarker bound to the passing molecule can still be accomplished. In another aspect, as shown in FIG. 3B, with a positive voltage applied and KCl concentrations less than 0.4 M in the experiment buffer, the measured current signals 308, when 312, 313, and 314 pass through the pore, are signals 309, 310, and 311, respectively. Passage of dsDNA alone causes current enhancement events (309) at KCl concentrations less than 0.4 M. This was shown in the published research by Smeets, Ralph M M, et al. "Salt dependence of ion transport and DNA translocation through solid-state nanopores." Nano Letters 6.1 (2006): 89-95. Hence, the signal 309 can be differentiated from 310 and 311 by the event amplitude direction (polarity) relative to the open channel baseline current level (308), in addition to the three signals commonly having different amounts of the current shift (i.e., signal shift height relative to the open pore baseline current) and/or the duration of the current shift (width), or by any other feature in the signal that differentiates the three event types. In another aspect, as shown in FIG. 3C, with a negative voltage applied and KCl concentrations less than 0.4 M in the experiment buffer, the negative measured current signals 315, when 319, 320, and 321 pass through the pore, are signals 316, 317, and 318, respectively. Compared to signals 309, 310, and 311 with a positive voltage, the signals 316, 317, and 318 have the opposite polarity since the applied voltage has the opposite (negative) polarity. In all aspects of the embodiments in FIGS. 3A, 3B, and 3C, the sensor comprises electrodes, which are connected to power sources and can detect the current. Either one or both of the electrodes, therefore, serve as a "sensor." In this embodiment, a voltage-clamp or a patch-clamp is used to simultaneously supply a voltage across the pore and measure the current through the pore.

In some aspects, an agent 106 as shown in FIG. 1 is added to the complex to aid detection. This agent is capable of binding to the target molecule or the ligand/target molecule complex. In one aspect, the agent includes a charge, either negative or positive, to facilitate detection. In another aspect, the agent adds size to facilitate detection. In another aspect, the agent includes a detectable label, such as a fluorophore.

In this context, an identification of status (iii) indicates that a polymer-fusion molecule-target molecule complex has formed. In other words, the target molecule is detected.

Particle Detection

The present disclosure also provides, in some aspects, methods and systems for detecting, quantitating, and measuring particles such as proteins, protein aggregates, oligomers, or protein/DNA complexes, or cells and microorganisms, including viruses, bacteria, and cellular aggregates.

In some aspects, the pore within the structure that separates the device into two volumes has a size that allows particles, such as viruses, bacteria, cells, or cellular aggregates, to pass through. A ligand that is capable of binding to a target particle to be detected or quantitated can be included in the solution in the nanopore device such that the ligand can bind to the unique target particle and the polymer scaffold through a binding domain and a binding motif to form a complex. Many such particles have unique markers on their surfaces that can be specifically recognized by a ligand. For instance, tumor cells can have tumor antigens expressed on the cell surface, and bacterial cells can have endotoxins attached on the cell membrane.

When the formed complex in a solution loaded into the nanopore device is moved along with the polymer scaffold to pass through the pore, the binding status of the complex within or adjacent to the pore can be detected such that the target microorganisms bound to the ligands can be identified using methods similar to the molecular detection methods described elsewhere in the disclosure.

Polymer Scaffold

A polymer scaffold suitable for use in the present technology is a scaffold that can be loaded into a nanopore device and passed through the pore from one end to the other.

Non-limiting examples of polymers include nucleic acids, such as deoxyribonucleic acid (DNA), ribonucleic acid (RNA), or peptide nucleic acid (PNA), dendrimers, and linearized proteins or peptides. In some aspects, the DNA or RNA can be single-stranded or double-stranded, or can be a DNA/RNA hybrid molecule.

In one aspect, the polymer is synthetic or chemically modified. Chemical modification can help to stabilize the polymer, add charges to the polymer to increase mobility, maintain linearity, or add or modify the binding specificity. In some aspects, the chemical modification is acetylation, methylation, summolation, oxidation, phosphorylation, glycosylation, or the addition of biotin.

In some aspects, the polymer is electrically charged. DNA, RNA, modified-PNA and proteins are typically charged under physiological conditions. Such polymers can be further modified to increase or decrease the carried charge. Other polymers can be modified to introduce charges. Charges on the polymer can be useful for driving the polymer to pass through the pore of a nanopore device. For instance, a charged polymer can move across the pore by virtue of an application of voltage across the pore.

In some aspects, when charges are introduced to the polymer, the charges can be added at the ends of the polymer. In some aspects, the charges are spread over the polymer.

In one embodiment, each unit of the charged polymer is charged at the pH selected. In another embodiment, the charged polymer includes sufficient charged units to be pulled into and through the pore by electrostatic forces. For example, a peptide containing sufficient entities can be charged at a selected pH (lysine, aspartic acid, glutamic acid, etc.) so as to be used in the devices and methods described herein. Likewise, a co-polymer comprising methacrylic acid and ethylene is a charged polymer for the purposes of this invention if there is sufficient charged carboxylate groups of the methacrylic acid residue to be used in the devices and methods described herein. In one embodiment, the charged polymer includes one or more charged units at or close to one terminus of the polymer. In another embodiment, the charged polymer includes one or more charged units at or close to both termini of the polymer. One co-polymer example is a DNA wrapped around protein (e.g. DNA/nucleosome). Another example of a co-polymer is a linearized protein conjugated to DNA at the N- and C-terminus.

Binding Motifs and Binding Domains

For nucleic acids and polypeptides as the polymer scaffold, binding can be due to a nucleotide or peptide region or sequence that is recognizable by a binding domain. In some embodiments, the binding domain is a peptide sequence forming a functional portion of a protein, although the binding domain does not have to be a protein. For nucleic acids, for instance, there are proteins that recognize and bind to DNA in a non-sequence specific manner.

In some aspects, the binding motif includes a chemical modification that causes or facilitates recognition and binding by a binding domain. For example, methylated DNA sequences can be recognized by transcription factors, DNA methyltransferases or methylation repair enzymes. In other embodiments, biotin may be incorporated into, and recognized by, avidin family members. In such embodiments, biotin forms the binding motif and avidin or an avidin family member is the binding domain.

Molecules, in particular proteins, that are capable of specifically recognizing nucleotide sequence are known in the art. For instance, protein domains such as helix-turn-helix, a zinc finger, a leucine zipper, a winged helix, a winged helix turn helix, a helix-loop-helix and an HMG-box, are known to be able to bind to nucleotide sequences.

In some aspects, the binding domains can be or aptamers (e.g., DNA, RNA, protein, or combinations thereof) that recognize nucleic acid or protein sequence.

In some aspects, the binding domains are one or more of DNA binding proteins (e.g., zinc finger proteins), antibody fragments (Fab), chemically synthesized binders or a chemical modification (i.e., reactive moieties) in the synthetic polymer (e.g., thiolate, biotin, amines, carboxylates).

In some aspects, the fusion molecules are permanently attached to the scaffold to prevent them from dissociating from the scaffold once bound. One example of doing this is to use formaldehyde to chemically cross-link a protein DNA binding domain to the scaffold (e.g. RecA protein to DNA).

Target Molecule/Particles and Ligands

In the present technology, a target molecule or particle is detected or quantitated by virtue of its binding to a ligand in a fusion molecule that binds to a polymer scaffold. A target molecule or particle and a corresponding binding ligand can recognize and bind each other. For a particle, there can be surface molecules or markers suitable for a ligand to bind (therefore the marker and the ligand form a binding pair).

Examples of binding pairs that enable binding between a target molecule or a molecule on a particle include, but are not limited to, antigen/antibody (or antibody fragment); hormone, neurotransmitter, cytokine, growth factor or cell recognition molecule/receptor; and ion or element/chelate agent or ion binding protein, such as a calmodulin. The binding pairs can also be single-stranded nucleic acids having complementary sequences, enzymes and substrates, members of protein complex that bind each other, enzymes and cofactors, enzymes and one or more of their inhibitors (allosteric or otherwise), nucleic acid/protein, or cells or proteins detectable by cysteine-constrained peptides.

In some embodiments, the ligand is a protein, protein scaffold, peptide, aptamer (DNA or protein), nucleic acid (DNA or RNA), antibody fragment (Fab), chemically synthesized molecule, chemically reactive functional group or any other suitable structure that forms a binding pair with a target molecule.

Therefore, any target molecule in need of detection or quantitation, such as proteins, peptides, nucleic acids, chemical compounds, ions, and elements, can find a corresponding binding ligand. For the majority of proteins and nucleic acids, an antibody or a complementary sequence, or an aptamer can be readily prepared.

Likewise, binding ligands (such as antibodies and aptamers) can be readily found or prepared for particles, such as protein complexes and protein aggregates, protein/nucleic acid complexes, fragmented or fully assembled viruses, bacteria, cells, and cellular aggregates.

Fusion Molecule

A "fusion molecule" is intended to mean a molecule or complex that contains two functional regions, a binding domain and a ligand. The binding domain is capable of binding to a polymer scaffold, and the ligand is capable of binding to a target molecule.

In some aspects, the fusion molecule is prepared by linking the two regions with a bond or force. Such a bond and force can be, for instance, a covalent bond, a hydrogen bond, an ionic bond, a metallic bond, van der Walls force, hydrophobic interaction, or planar stacking interaction.

In some aspects, the fusion molecule, such as a fusion protein, can be expressed as a single molecule from a recombinant coding nucleotide. In some aspects, the fusion molecule is a natural molecule having a binding domain and a ligand suitable for use in the present technology.

Many options exist for connecting the binding domain with the ligand to form the fusion molecule. For example, the components may be connected via chemical coupling through functionalized linkers such as free amine, carboxylate coupling, thiolate, hydrazide, or azide (click) chemistry or the binding domain and the ligand may form one continuous transcript.

Figure 2:
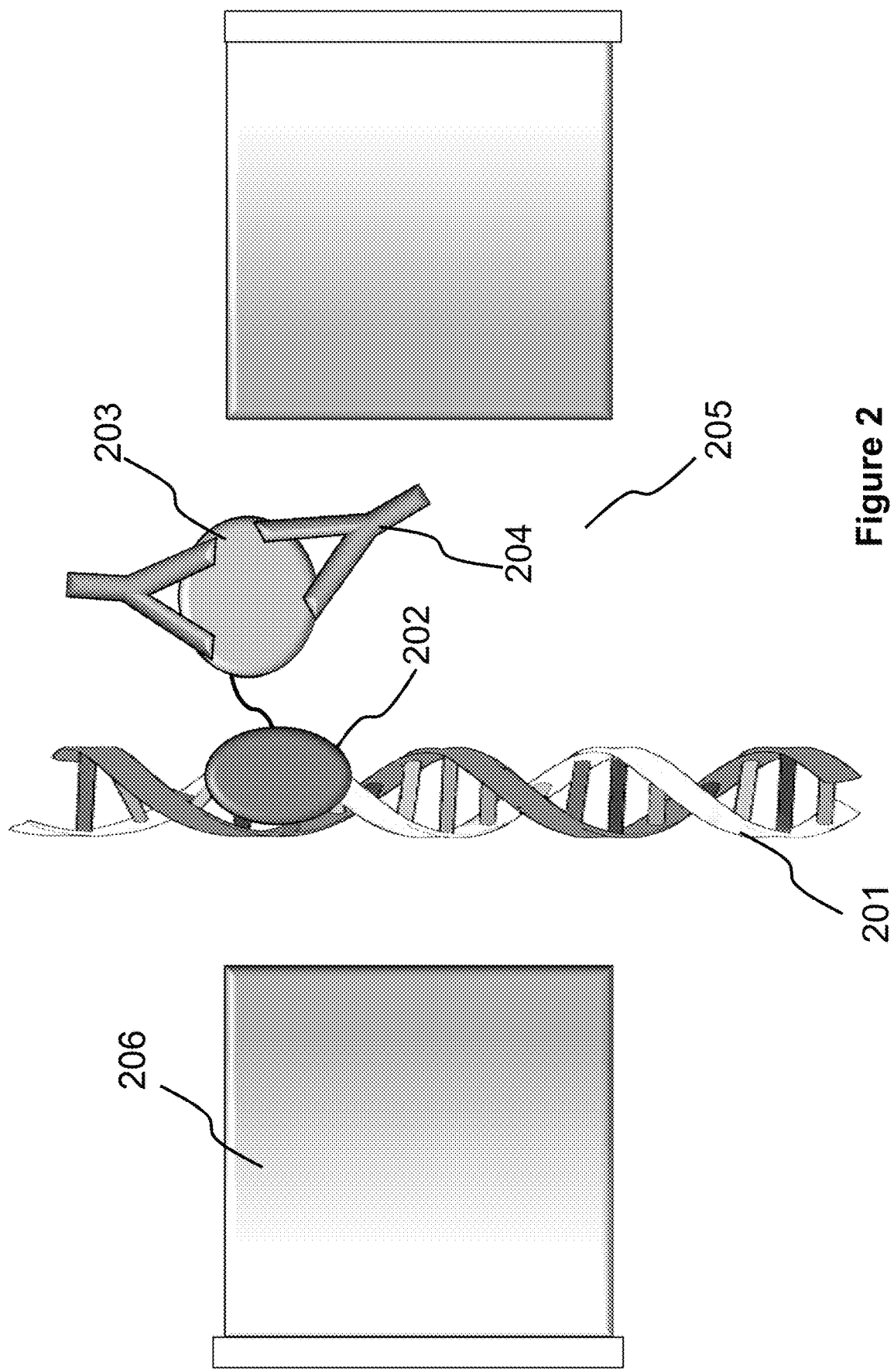
FIG. 2 provides the illustration of a more specific example, where a double-stranded DNA is used as the polymer scaffold, and a human immunodeficiency virus (HIV) envelope protein is used as the ligand (comprising target binding domain), and RecA is used as the DNA binding domain. The combination is used to detect an anti-HIV antibody.

FIG. 2 illustrates a more specific embodiment of the system shown in FIG. 1. In FIG. 2, the fusion molecule is a chimeric protein that includes a RecA protein 202 and a human immunodeficiency virus (HIV) envelop protein 203. The RecA protein 202 can bind to and form filaments on dsDNA 201, and stay stably bound when coupled with ATP-gamma-S (a non-hydrolyzable ATP analog); the HIV envelop protein 203 can bind to an anti-HIV antibody 204 which can be present in a biological sample (e.g., a blood sample from a patient) for detection.

When the double-stranded DNA 201 passes through a pore 205 of a nanopore device 206, the nanopore device 206 can detect whether a fusion molecule is bound to the DNA 201 and whether the bound fusion molecule binds to an anti-HIV antibody 204.

Measurement of Affinity of Binding

The present technology can be used also for measuring the binding affinity between two molecules and to determine other binding dynamics. For instance, after the binding motif passes through the pore of a nanopore device, the device can be reconfigured to reverse the moving direction of the polymer scaffold (as described below) such that the binding motif can pass through the pore again.

Before the binding motif enters the pore again, one can change the conditions in the sample that is loaded into the nanopore device. For instance, changing the condition can be one or more of removing the target molecule from the sample, adding an agent that competes with the target molecule or the ligand for binding, and changing the pH, salt, or temperature.

Under the changed conditions, the binding motif may be passed through the pore again. Therefore, whether the target molecule is still bound to the fusion molecule can be detected to determine how the changed conditions impact the binding.

In some aspects, once the binding motif is in the pore, it is retained there while the conditions are changed, and thus the impact of the changed conditions can be measured in situ.

Signal Boosting

A method of signal boosting involves having many fusion proteins bound to the same scaffold, which will allow more robust sensing by the sensor. Having many fusions bound close together will allow more than one fusion to be in the pore at once generating greater impedance, or the multitude of bound fusion proteins will influence the scaffold in a measurable manner, e.g. increasing translocation time or amplitude of events. Binding of the target analyte will influence these measurable parameters by an even greater degree providing a unique event signature enabling biomarker detection.

Figure 4A:
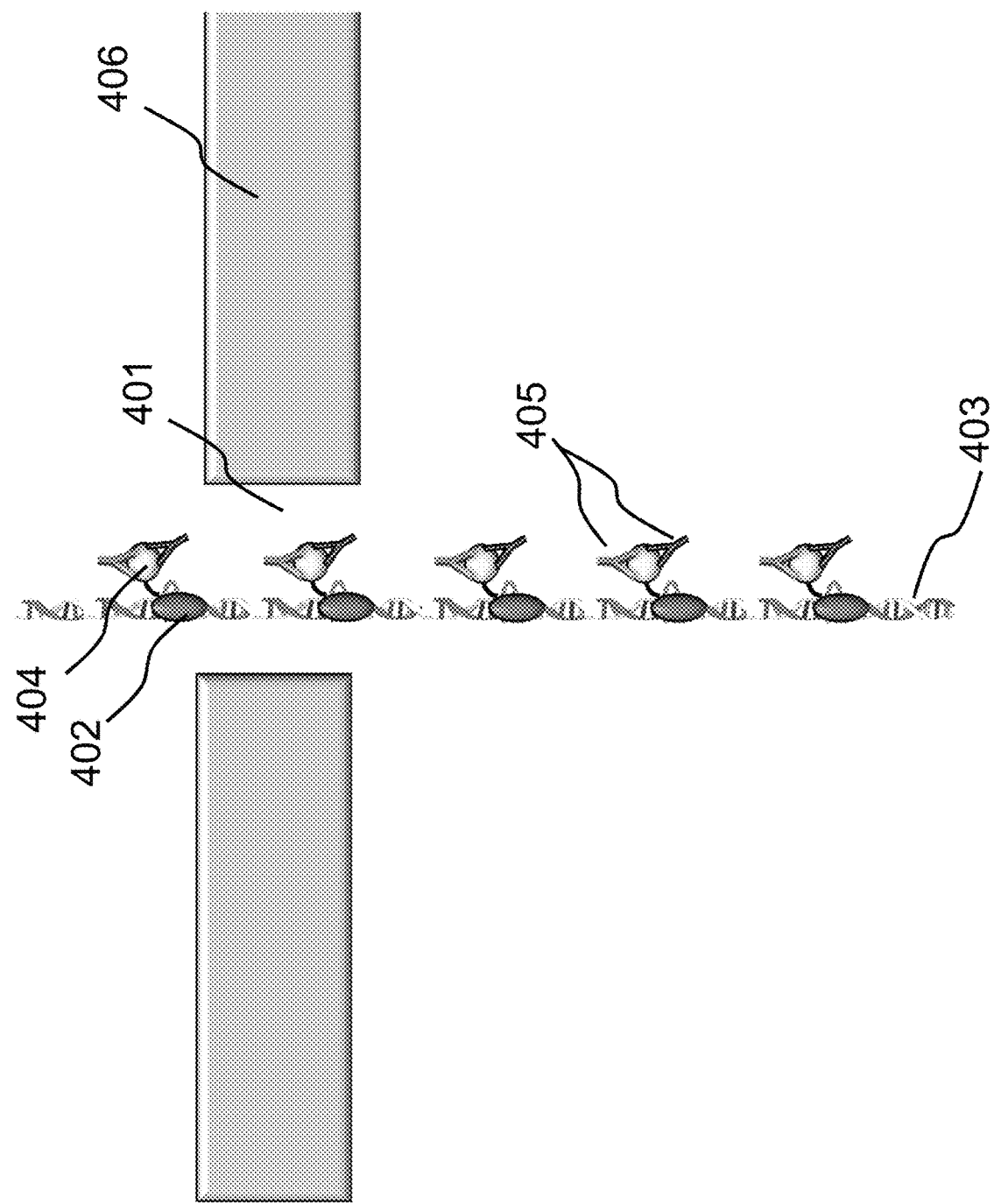
FIG. 4A illustrates the capability of the present technology to boost signal by including many binding motifs in the polymer scaffold. Such signal boost can be accomplished with one nanopore or more than one nanopore.

With such a setting, a single polymer scaffold can be used to bind multiple of target molecules or target microorganisms (e.g. bacterium or virus), or target cells (e.g. circulating tumor cells). FIG. 4A illustrates such a method. Here, a double-stranded DNA 403 is used as the polymer scaffold that binds RecA 402 connected to HIV Env protein 404 to create the fusion molecule that binds scaffold in a non-sequence specific manner. When the DNA passes through a nanopore device 406 that has a pore 401 the binding status of each of the binding motifs is detected. Here, HIV specific antibody biomarkers are detected 405

Assay Multiplexing

A method of multiplexing includes assaying a collection of different scaffold molecules during a test, with each different scaffold associating fusion molecule(s) that have different ligands. To determine what target molecules are in solution, the different scaffolds are labeled with an identification modification such that the sensor can identify what each particular scaffold tests for. For example, an HIV scaffold can be differentiated from and HCV scaffold by using "scaffold ID molecules". This can be accomplished, for example, by barcoding each type of scaffold with polyethylene glycol molecules of varying lengths or sizes.

Figure 4B:
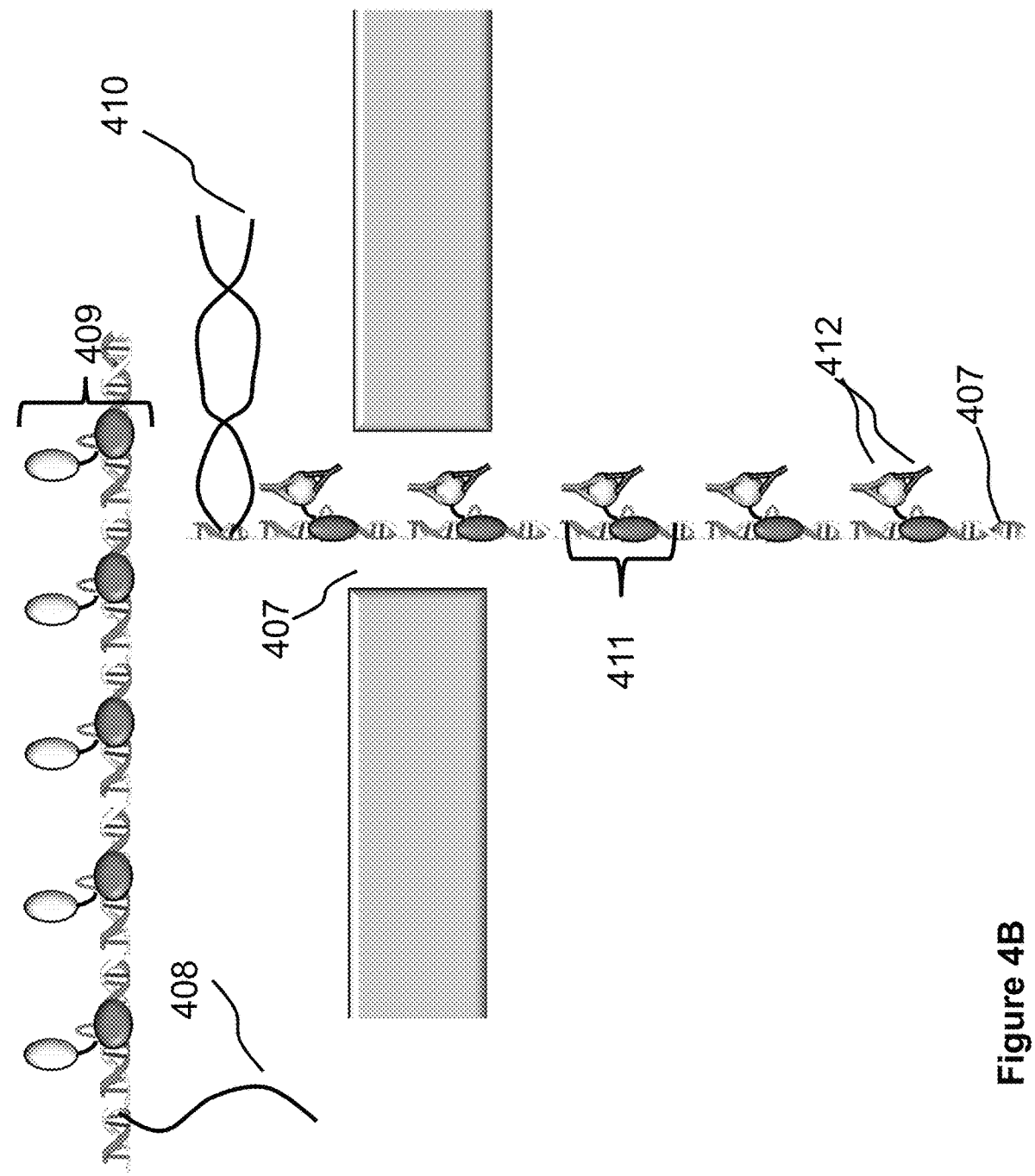
FIG. 4B illustrates the capability of the present technology to multiplex by bar coding scaffolds. This allows for the detection of more than one analyte in a test sample.

With such a setting, a single polymer scaffold can be used to detect one target molecule or target microorganism (e.g. bacterium or virus), or target cell (e.g. circulating tumor cells), and a second polymer can detect a different target. Each scaffold has a different PEG barcode. FIG. 4B illustrates such a method. Here, a double-stranded DNA scaffold 407 containing a single PEG 408 is pre-complexed with a fusion molecule that detects HIV 409. A second scaffold containing a double PEG 410 is pre-complexed with a fusion molecule that detects HCV 411. The different PEG labelings allow the scaffold to be differentiated from each other. The fusions are cross-linked to their respective scaffolds so they are permanently bound. When the DNA passes through a nanopore device 407 the binding status of each scaffold is detected. This allows both scaffolds to be assayed with the same test sample. Here the test would be positive for HCV antibody biomarker 412, but negative for HIV.

Nanopore Devices

A nanopore device, as provided, includes at least a pore that forms an opening in a structure separating an interior space of the device into two volumes, and at least a sensor configured to identify objects (for example, by detecting changes in parameters indicative of objects) passing through the pore.

The pore(s) in the nanopore device are of a nano scale or micro scale. In one aspect, each pore has a size that allows a small or large molecule or microorganism to pass. In one aspect, each pore is at least about 1 nm in diameter. Alternatively, each pore is at least about 2 nm, 3 nm, 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 25 nm, 30 nm, 35 nm, 40 nm, 45 nm, 50 nm, 60 nm, 70 nm, 80 nm, 90 nm, or 100 nm in diameter.

In one aspect, the pore is no more than about 100 nm in diameter. Alternatively, the pore is no more than about 95 nm, 90 nm, 85 nm, 80 nm, 75 nm, 70 nm, 65 nm, 60 nm, 55 nm, 50 nm, 45 nm, 40 nm, 35 nm, 30 nm, 25 nm, 20 nm, 15 nm, or 10 nm in diameter.

In some aspects, each pore is at least about 100 nm, 200 nm, 500 nm, 1000 nm, 2000 nm, 3000 nm, 5000 nm, 10000 nm, 20000 nm, or 30000 nm in diameter. In one aspect, the pore is no more than about 100000 nm in diameter. Alternatively, the pore is no more than about 50000 nm, 40000 nm, 30000 nm, 20000 nm, 10000 nm, 9000 nm, 8000 nm, 7000 nm, 6000 nm, 5000 nm, 4000 nm, 3000 nm, 2000 nm, or 1000 nm in diameter.

In one aspect, the pore has a diameter that is between about 1 nm and about 100 nm, or alternatively between about 2 nm and about 80 nm, or between about 3 nm and about 70 nm, or between about 4 nm and about 60 nm, or between about 5 nm and about 50 nm, or between about 10 nm and about 40 nm, or between about 15 nm and about 30 nm.

In some aspects, the pore(s) in the nanopore device are of a larger scale for detecting large microorganisms or cells. In one aspect, each pore has a size that allows a large cell or microorganism to pass. In one aspect, each pore is at least about 100 nm in diameter. Alternatively, each pore is at least about 200 nm, 300 nm, 400 nm, 500 nm, 600 nm, 700 nm, 800 nm, 900 nm, 1000 nm, 1100 nm, 1200 nm, 1300 nm, 1400 nm, 1500 nm, 1600 nm, 1700 nm, 1800 nm, 1900 nm, 2000 nm, 2500 nm, 3000 nm, 3500 nm, 4000 nm, 4500 nm, or 5000 nm in diameter.

In one aspect, the pore is no more than about 100,000 nm in diameter. Alternatively, the pore is no more than about 90,000 nm, 80,000 nm, 70,000 nm, 60,000 nm, 50,000 nm, 40,000 nm, 30,000 nm, 20,000 nm, 10,000 nm, 9000 nm, 8000 nm, 7000 nm, 6000 nm, 5000 nm, 4000 nm, 3000 nm, 2000 nm, or 1000 nm in diameter.

In one aspect, the pore has a diameter that is between about 100 nm and about 10000 nm, or alternatively between about 200 nm and about 9000 nm, or between about 300 nm and about 8000 nm, or between about 400 nm and about 7000 nm, or between about 500 nm and about 6000 nm, or between about 1000 nm and about 5000 nm, or between about 1500 nm and about 3000 nm.

In some aspects, the nanopore device further includes means to move a polymer scaffold across the pore and/or means to identify objects that pass through the pore. Further details are provided below, described in the context of a two-pore device.

Compared to a single-pore nanopore device, a two-pore device can be more easily configured to provide good control of speed and direction of the movement of the polymer across the pores during sensing.

In one embodiment, the nanopore device includes a plurality of chambers, each chamber in communication with an adjacent chamber through a pore. Among these pores, two pores, namely a first pore and a second pore, are placed so as to allow at least a portion of a polymer to move out of the first pore and into the second pore. Further, the device includes a sensor capable of identifying the polymer during the movement. In one aspect, the identification entails identifying individual components of the polymer. In another aspect, the identification entails identifying fusion molecules and/or target molecules bound to the polymer. When a single sensor is employed, the single sensor may include two electrodes placed at both ends of a pore to measure an ionic current across the pore. In another embodiment, the single sensor comprises a component other than electrodes.

In one aspect, the device includes three chambers connected through two pores. Devices with more than three chambers can be readily designed to include one or more additional chambers on either side of a three-chamber device, or between any two of the three chambers. Likewise, more than two pores can be included in the device to connect the chambers.

In one aspect, there can be two or more pores between two adjacent chambers, to allow multiple polymers to move from one chamber to the next simultaneously. Such a multi-pore design can enhance throughput of polymer analysis in the device.

In some aspects, the device further includes means to move a polymer from one chamber to another. In one aspect, the movement results in loading the polymer across both the first pore and the second pore at the same time. In another aspect, the means further enables the movement of the polymer, through both pores, in the same direction.

For instance, in a three-chamber two-pore device (a "two-pore" device), each of the chambers can contain an electrode for connecting to a power supply so that a separate voltage can be applied across each of the pores between the chambers.

In accordance with one embodiment of the present disclosure, provided is a device comprising an upper chamber, a middle chamber and a lower chamber, wherein the upper chamber is in communication with the middle chamber through a first pore, and the middle chamber is in communication with the lower chamber through a second pore. Such a device may have any of the dimensions or other characteristics previously disclosed in U.S. Publ. No. 2013-0233709, entitled Dual-Pore Device, which is herein incorporated by reference in its entirety.

Figure 5A:
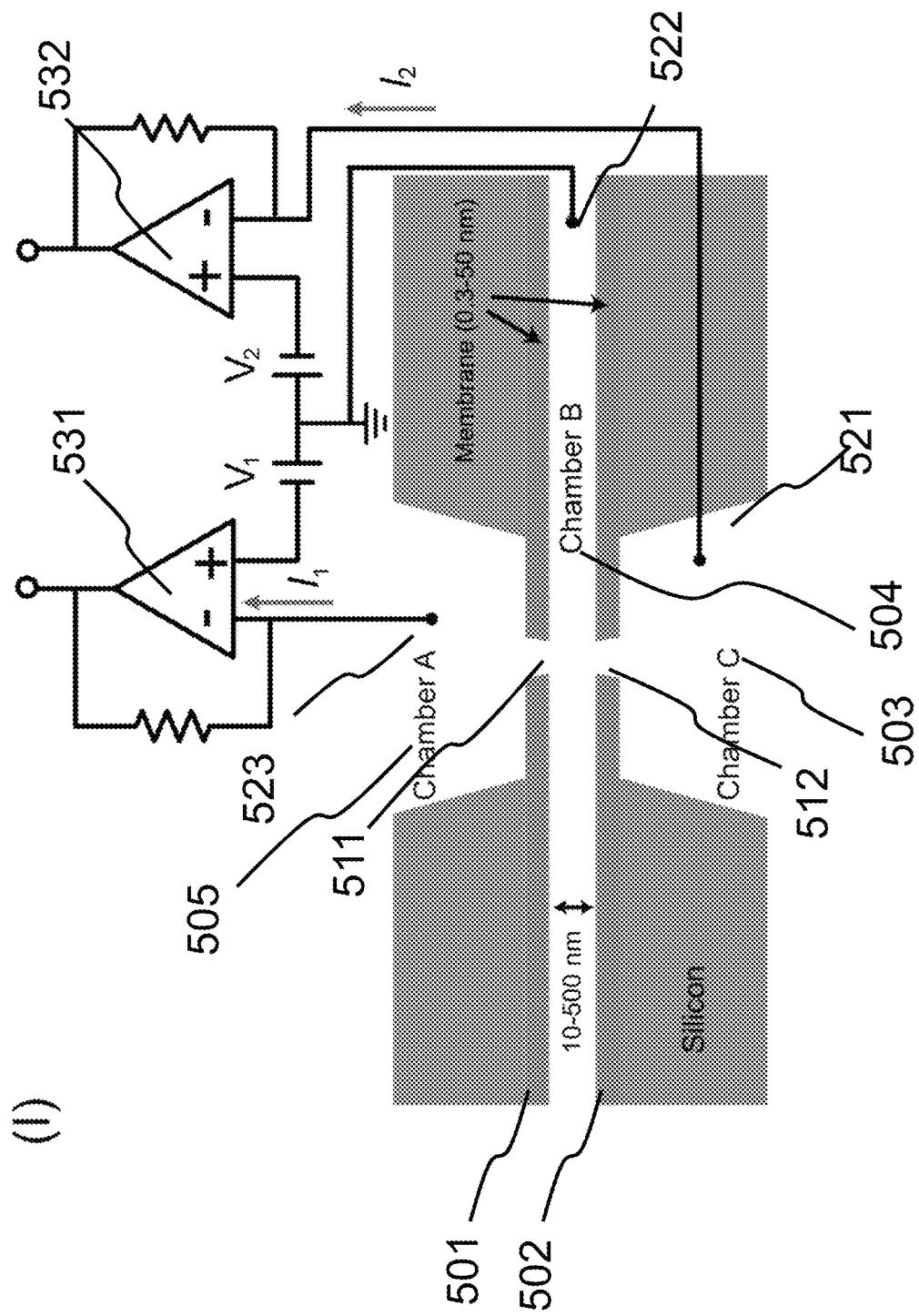
FIGS. 5A, 5B, and 5C illustrate a nanopore device with at least two pores separating multiple chambers.

In some embodiments as shown in FIG. 5A, the device includes an upper chamber 505 (Chamber A), a middle chamber 504 (Chamber B), and a lower chamber 503 (Chamber C). The chambers are separated by two separating layers or membranes (501 and 502) each having a separate pore (511 or 512). Further, each chamber contains an electrode (521, 522 or 523) for connecting to a power supply. The annotation of upper, middle and lower chamber is in relative terms and does not indicate that, for instance, the upper chamber is placed above the middle or lower chamber relative to the ground, or vice versa.

Each of the pores 511 and 512 independently has a size that allows a small or large molecule or microorganism to pass. In one aspect, each pore is at least about 1 nm in diameter. Alternatively, each pore is at least about 2 nm, 3 nm, 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 25 nm, 30 nm, 35 nm, 40 nm, 45 nm, 50 nm, 60 nm, 70 nm, 80 nm, 90 nm, or 100 nm in diameter.

In one aspect, the pore is no more than about 100 nm in diameter. Alternatively, the pore is no more than about 95 nm, 90 nm, 85 nm, 80 nm, 75 nm, 70 nm, 65 nm, 60 nm, 55 nm, 50 nm, 45 nm, 40 nm, 35 nm, 30 nm, 25 nm, 20 nm, 15 nm, or 10 nm in diameter.

In one aspect, the pore has a diameter that is between about 1 nm and about 100 nm, or alternatively between about 2 nm and about 80 nm, or between about 3 nm and about 70 nm, or between about 4 nm and about 60 nm, or between about 5 nm and about 50 nm, or between about 10 nm and about 40 nm, or between about 15 nm and about 30 nm.

In other aspects, each pore is at least about 100 nm, 200 nm, 500 nm, 1000 nm, 2000 nm, 3000 nm, 5000 nm, 10000 nm, 20000 nm, or 30000 nm in diameter. In one aspect, each pore is 50,000 nm to 100,000 nm in diameter. In one aspect, the pore is no more than about 100000 nm in diameter. Alternatively, the pore is no more than about 50000 nm, 40000 nm, 30000 nm, 20000 nm, 10000 nm, 9000 nm, 8000 nm, 7000 nm, 6000 nm, 5000 nm, 4000 nm, 3000 nm, 2000 nm, or 1000 nm in diameter.

In some aspects, the pore has a substantially round shape. "Substantially round", as used here, refers to a shape that is at least about 80 or 90% in the form of a cylinder. In some embodiments, the pore is square, rectangular, triangular, oval, or hexagonal in shape.

Each of the pores 511 and 512 independently has a depth (i.e., a length of the pore extending between two adjacent volumes). In one aspect, each pore has a depth that is least about 0.3 nm. Alternatively, each pore has a depth that is at least about 0.6 nm, 1 nm, 2 nm, 3 nm, 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 25 nm, 30 nm, 35 nm, 40 nm, 45 nm, 50 nm, 60 nm, 70 nm, 80 nm, or 90 nm.

In one aspect, each pore has a depth that is no more than about 100 nm. Alternatively, the depth is no more than about 95 nm, 90 nm, 85 nm, 80 nm, 75 nm, 70 nm, 65 nm, 60 nm, 55 nm, 50 nm, 45 nm, 40 nm, 35 nm, 30 nm, 25 nm, 20 nm, 15 nm, or 10 nm.

In one aspect, the pore has a depth that is between about 1 nm and about 100 nm, or alternatively, between about 2 nm and about 80 nm, or between about 3 nm and about 70 nm, or between about 4 nm and about 60 nm, or between about 5 nm and about 50 nm, or between about 10 nm and about 40 nm, or between about 15 nm and about 30 nm.

The nanopore extends through a membrane. In one example, the pore may be a protein channel inserted in a lipid bilayer membrane. Alternatively, it may be engineered by drilling, etching, or otherwise forming the pore through a solid-state substrate such as silicon dioxide, silicon nitride, grapheme, or layers formed of combinations of these or other materials. The length of the nanopore is sufficiently large so as to form a channel connecting two otherwise separate volumes.

In some such aspects, the length of each pore is greater than 100 nm, 200 nm, 300 nm, 400 nm, 500 nm, 600 nm, 700 nm, 800 nm, or 900 nm. In some aspects, the length of each pore is no more than 2000 nm or 1000 nm. For lengths greater than 200 nm, the nanopore is commonly referred to as a "nanochannel", though it may also still be referred to as a "nanopore".

In one aspect, the pores in two-pore devices are spaced apart at a distance that is between about 10 nm and about 1000 nm. In some aspects, the distance between the pores is greater than 1000 nm, 2000 nm, 3000 nm, 4000 nm, 5000 nm, 6000 nm, 7000 nm, 8000 nm, or 9000 nm. In some aspects, the pores are spaced no more than 30000 nm, 20000 nm, or 10000 nm apart. In one aspect, the distance is at least about 10 nm, or alternatively, at least about 20 nm, 30 nm, 40 nm, 50 nm, 60 nm, 70 nm, 80 nm, 90 nm, 100 nm, 150 nm, 200 nm, 250 nm, or 300 nm. In another aspect, the distance is no more than about 1000 nm, 900 nm, 800 nm, 700 nm, 600 nm, 500 nm, 400 nm, 300 nm, 250 nm, 200 nm, 150 nm, or 100 nm.

In yet another aspect, the distance between the pores is between about 20 nm and about 800 nm, between about 30 nm and about 700 nm, between about 40 nm and about 500 nm, or between about 50 nm and about 300 nm.

The two pores can be arranged in any position so long as they allow fluid communication between the chambers and have the prescribed size and distance between them. In one aspect, the pores are placed so that there is no direct blockage between them. Still, in one aspect, the pores are substantially coaxial, as illustrated in FIG. 5A.

In one aspect, as shown in FIG. 5A, the device, through the electrodes 521, 522, and 523 in the chambers 503, 504, and 505, respectively, is connected to one or more power supplies. In some aspects, the power supply includes a voltage-clamp or a patch-clamp, which can supply a voltage across each pore and measure the current through each pore independently. In this respect, the power supply and the electrode configuration can set the middle chamber to a common ground for both power supplies. In one aspect, the power supply or supplies are configured to apply a first voltage $V_1$ between the upper chamber 505 (Chamber A) and the middle chamber 504 (Chamber B), and a second voltage $V_2$ between the middle chamber 504 and the lower chamber 503 (Chamber C).

In some aspects, the first voltage $V_1$ and the second voltage $V_2$ are independently adjustable. In one aspect, the middle chamber is adjusted to be a ground relative to the two voltages. In one aspect, the middle chamber comprises a medium for providing conductance between each of the pores and the electrode in the middle chamber. In one aspect, the middle chamber includes a medium for providing a resistance between each of the pores and the electrode in the middle chamber. Keeping such a resistance sufficiently small relative to the nanopore resistances is useful for decoupling the two voltages and currents across the pores, which is helpful for the independent adjustment of the voltages.

Adjustment of the voltages can be used to control the movement of charged particles in the chambers. For instance, when both voltages are set in the same polarity, a properly charged particle can be moved from the upper chamber to the middle chamber and to the lower chamber, or the other way around, sequentially. In some aspects, when the two voltages are set to opposite polarity, a charged particle can be moved from either the upper or the lower chamber to the middle chamber and kept there.

The adjustment of the voltages in the device can be particularly useful for controlling the movement of a large molecule, such as a charged polymer, that is long enough to cross both pores at the same time. In such an aspect, the direction and the speed of the movement of the molecule can be controlled by the relative magnitude and polarity of the voltages as described below.

The device can contain materials suitable for holding liquid samples, in particular, biological samples, and/or materials suitable for nanofabrication. In one aspect, such materials include dielectric materials such as, but not limited to, silicon, silicon nitride, silicon dioxide, graphene, carbon nanotubes, $TiO_2$, $HfO_2$, $Al_2O_3$, or other metallic layers, or any combination of these materials. In some aspects, for example, a single sheet of graphene membrane of about 0.3 nm thick can be used as the pore-bearing membrane.

Figure 5C:
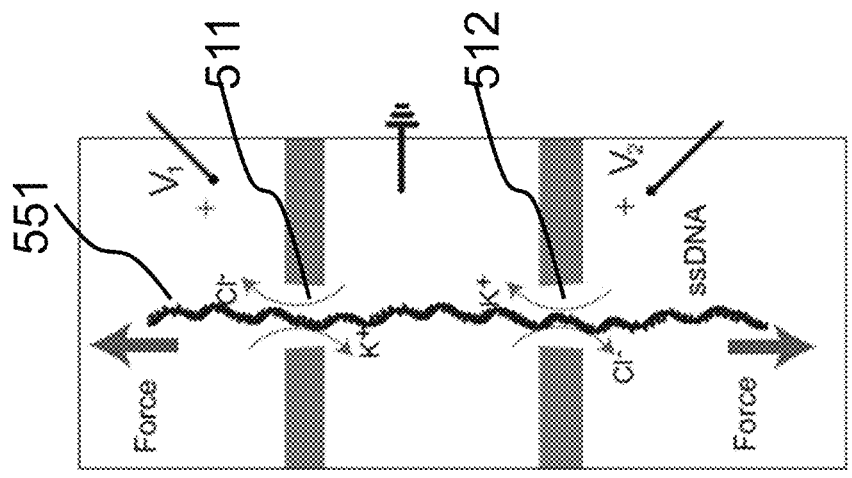
Figure 5B:
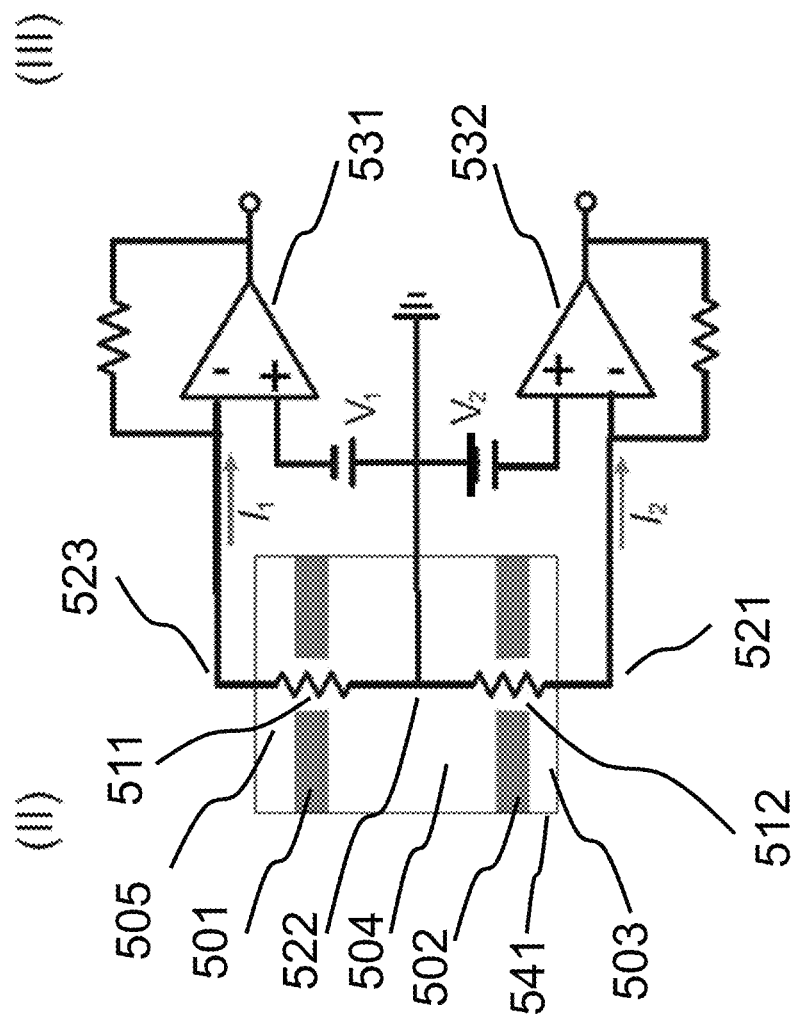

Devices that are microfluidic and that house two-pore microfluidic chip implementations can be made by a variety of means and methods. For a microfluidic chip comprised of two parallel membranes, both membranes can be simultaneously drilled by a single beam to form two concentric pores, though using different beams on each side of the membranes is also possible in concert with any suitable alignment technique. In general terms, the housing ensures sealed separation of Chambers A-C. In one aspect as shown in FIG. 5B, the housing would provide minimal access resistance between the voltage electrodes 521, 522, and 523 and the nanopores 511 and 512, to ensure that each voltage is applied principally across each pore.

In one aspect, the device includes a microfluidic chip (labeled as "Dual-pore chip") is comprised of two parallel membranes connected by spacers. Each membrane contains a pore drilled by a single beam through the center of the membrane. Further, the device preferably has a Teflon® housing for the chip. The housing ensures sealed separation of Chambers A-C and provides minimal access resistance for the electrode to ensure that each voltage is applied principally across each pore.

More specifically, the pore-bearing membranes can be made with transmission electron microscopy (TEM) grids with a 5-100 nm thick silicon, silicon nitride, or silicon dioxide windows. Spacers can be used to separate the membranes, using an insulator, such as SU-8, photoresist, PECVD oxide, ALD oxide, ALD alumina, or an evaporated metal material, such as Ag, Au, or Pt, and occupying a small volume within the otherwise aqueous portion of Chamber B between the membranes. A holder is seated in an aqueous bath that is comprised of the largest volumetric fraction of Chamber B. Chambers A and C are accessible by larger diameter channels (for low access resistance) that lead to the membrane seals.

A focused electron or ion beam can be used to drill pores through the membranes, naturally aligning them. The pores can also be sculpted (shrunk) to smaller sizes by applying a correct beam focusing to each layer. Any single nanopore drilling method can also be used to drill the pair of pores in the two membranes, with consideration to the drill depth possible for a given method and the thickness of the membranes. Predrilling a micro-pore to a prescribed depth and then a nanopore through the remainder of the membranes is also possible to further refine the membrane thickness.

In another aspect, the insertion of biological nanopores into solid-state nanopores to form a hybrid pore can be used in either or both pores in the two-pore method. The biological pore can increase the sensitivity of the ionic current measurements, and is useful when only single-stranded polynucleotides are to be captured and controlled in the two-pore device, e.g., for sequencing.

By virtue of the voltages present at the pores of the device, charged molecules can be moved through the pores between chambers. Speed and direction of the movement can be controlled by the magnitude and polarity of the voltages. Further, because each of the two voltages can be independently adjusted, the direction and speed of the movement of a charged molecule can be finely controlled in each chamber.

One example concerns a charged polymer scaffold, such as a DNA, having a length that is longer than the combined distance that includes the depth of both pores plus the distance between the two pores. For example, a 1000 bp dsDNA is about 340 nm in length, and would be substantially longer than the 40 nm spanned by two 10 nm-deep pores separated by 20 nm. In a first step, the polynucleotide is loaded into either the upper or the lower chamber. By virtue of its negative charge under a physiological condition at a pH of about 7.4 and in a buffered ionic solution (e.g., 1M KCl), the polynucleotide can be moved across a pore on which a voltage is applied. Therefore, in a second step, two voltages, in the same polarity and at the same or similar magnitudes, are applied to the pores to move the polynucleotide across both pores sequentially.

At about the time when the polynucleotide reaches the second pore, one or both of the voltages can be changed. Since the distance between the two pores is selected to be shorter than the length of the polynucleotide, when the polynucleotide reaches the second pore, it is also in the first pore. A prompt change of polarity of the voltage at the first pore, therefore, will generate a force that pulls the polynucleotide away from the second pore as illustrated in FIG. 5C.

Assuming that the two pores have identical voltage-force influence and $|V_1|=|V_2|+\delta V$, the value $\delta V>0$ (or $<0$) can be adjusted for tunable motion in the $V_1$ (or $V_2$) direction. In practice, although the voltage-induced force at each pore will not be identical with $V_1=V_2$, calibration experiments can identify the appropriate bias voltage that will result in equal pulling forces for a given two-pore chip; and variations around that bias voltage can then be used for directional control.

If, at this point, the magnitude of the voltage-induced force at the first pore is less than that of the voltage-induced force at the second pore, then the polynucleotide will continue crossing both pores towards the second pore, but at a lower speed. In this respect, it is readily appreciated that the speed and direction of the movement of the polynucleotide can be controlled by the polarities and magnitudes of both voltages. As will be further described below, such a fine control of movement has broad applications.

Accordingly, in one aspect, provided is a method for controlling the movement of a charged polymer through a nanopore device. The method entails (a) loading a sample comprising a charged polymer in one of the upper chamber, middle chamber or lower chamber of the device of any of the above embodiments, wherein the device is connected to one or more power supplies for providing a first voltage between the upper chamber and the middle chamber, and a second voltage between the middle chamber and the lower chamber; (b) setting an initial first voltage and an initial second voltage so that the polymer moves between the chambers, thereby locating the polymer across both the first and second pores; and (c) adjusting the first voltage and the second voltage so that both voltages generate force to pull the charged polymer away from the middle chamber (voltage-competition mode), wherein the two voltages are different in magnitude, under controlled conditions, so that the charged polymer moves across both pores in either direction and in a controlled manner.

To establish the voltage-competition mode in step (c), the relative force exerted by each voltage at each pore is to be determined for each two-pore device used, and this can be done with calibration experiments by observing the influence of different voltage values on the motion of the polynucleotide, which can be measured by sensing known-location and detectable features in the polynucleotide, with examples of such features being the fusion and possibly also the target molecules bound at known sites on the polymeric scaffold as described in this application. If the forces are equivalent at each common voltage, for example, then using the same voltage value at each pore (with common polarity in upper and lower chambers relative to grounded middle chamber) creates a zero net motion in the absence of thermal agitation (the presence and influence of Brownian motion is discussed below). If the forces are not equivalent at each common voltage, achieving equal forces involves the identification and use of a larger voltage at the pore that experiences a weaker force at the common voltage. Calibration for voltage-competition mode can be done for each two-pore device, and for specific charged polymers or molecules whose features influence the force when passing through each pore.

In one aspect, the sample containing the charged polymer is loaded into the upper chamber and the initial first voltage is set to pull the charged polymer from the upper chamber to the middle chamber and the initial second voltage is set to pull the polymer from the middle chamber to the lower chamber. Likewise, the sample can be initially loaded into the lower chamber, and the charged polymer can be pulled to the middle and the upper chambers.

In another aspect, the sample containing the charged polymer is loaded into the middle chamber; the initial first voltage is set to pull the charged polymer from the middle chamber to the upper chamber; and the initial second voltage is set to pull the charged polymer from the middle chamber to the lower chamber.

In one aspect, the adjusted first voltage and second voltage at step (c) are about 10 times to about 10,000 times as high, in magnitude, as the difference/differential between the two voltages. For instance, the two voltages can be 90 mV and 100 mV, respectively. The magnitude of the two voltages, about 100 mV, is about 10 times of the difference/differential between them, 10 mV. In some aspects, the magnitude of the voltages is at least about 15 times, 20 times, 25 times, 30 times, 35 times, 40 times, 50 times, 100 times, 150 times, 200 times, 250 times, 300 times, 400 times, 500 times, 1000 times, 2000 times, 3000 times, 4000 times, 5000 times, 6000 times, 7000 times, 8000 times or 9000 times as high as the difference/differential between them. In some aspects, the magnitude of the voltages is no more than about 10000 times, 9000 times, 8000 times, 7000 times, 6000 times, 5000 times, 4000 times, 3000 times, 2000 times, 1000 times, 500 times, 400 times, 300 times, 200 times, or 100 times as high as the difference/differential between them.

In one aspect, real-time or on-line adjustments to the first voltage and the second voltage at step (c) are performed by active control or feedback control using dedicated hardware and software, at clock rates up to hundreds of megahertz. Automated control of the first or second or both voltages is based on feedback of the first or second or both ionic current measurements.

Sensors

As discussed above, in various aspects, the nanopore device further includes one or more sensors to carry out the identification of the binding status of the binding motifs.

The sensors used in the device can be any sensor suitable for identifying a molecule or particle, such as a polymer. For instance, a sensor can be configured to identify the polymer, features on the polymer, or tagging molecules by measuring a current, a voltage, a pH value, an optical feature, or residence time associated with the polymer. In other aspects, the sensor may be configured to identify one or more individual components of the polymer or one or more components bound to the polymer. The sensor may be formed of any component configured to detect a change in a measurable parameter where the change is indicative of the polymer, a component of the polymer, or preferably, a component bound to the polymer. In one aspect, the sensor includes a pair of electrodes placed at two sides of a pore to measure an ionic current across the pore when a molecule or particle, in particular a polymer, moves through the pore. In certain aspects, the ionic current across the pore changes measurably when a polymer segment passing through the pore is bound to a fusion molecule and/or fusion molecule-target molecule complex. Such changes in current may vary in predictable, measurable ways corresponding with, for example, the presence, absence, and/or size of the fusion molecules and target molecules present.

In one embodiment, the sensor measures an optical feature of the polymer, a component (or unit) of the polymer, or a component bound to the polymer. One example of such measurement includes the identification of an absorption band unique to a particular unit by infrared (or ultraviolet) spectroscopy.

When residence time measurements are used, the size of the component can be correlated to the specific component based on the length of time it takes to pass through the sensing device.

Still further, in embodiments directed towards detecting units of the polymer, the sensor can include an enzyme distal to the sensing device, where the enzyme is capable of separating the terminal unit of the polymer from the penultimate unit, thereby providing for a single molecular unit of the polymer. The single molecule, such as a single nucleotide or an amino acid, can then translocate through the pore and may or may not be detected. However, when the enzyme encounters a bound target molecule, the enzyme will not be able to cleave the penultimate unit, and therefore will become stalled or will skip to the next available cleavage sites, thus releasing a fragment that has a comparable size difference from a single unit and is thus detectable. Detection can be done with sensors as described in this application or detected with methods such as mass spectrometry. Methods for measuring such units are known in the art and include those developed using nano-electromechanical systems technology (see, e.g., Hanay M. S., et al., "Single-protein nanomechanical mass spectrometry in real time," *Nat Nano*, Vol. 7, No. 9, pp. 602-608, 2012.). The results of such analysis can be compared to those of the sensing device to confirm the correctness of the analysis.

In some embodiments, the sensor is functionalized with reagents that form distinct non-covalent bonds with each association site or each associated target molecule. In this respect, the gap is large enough to allow effective measuring. For instance, when a sensor is functionalized with reagents to detect a feature on DNA that is 5 nm on a dsDNA scaffold, a 7.5 nm gap can be used, because DNA is 2.5 nm wide.

Tunnel sensing with a functionalized sensor is termed "recognition tunneling." Using current technology, a Scanning Tunneling Microscope (STM) with recognition tunneling identifies a DNA base flanked by other bases in a short DNA oligomer. As has been described, recognition tunneling can provide a "universal reader" designed to hydrogen-bond in a unique orientation to molecules that a user desires to be detected. Most reported is the identification of nucleic acids; however, it is herein modified to be employed to detect target molecules on a scaffold.

A limitation with the conventional recognition tunneling is that it can detect only freely diffusing molecules that randomly bind in the gap, or that happen to be in the gap during microscope motion, with no method of explicit capture in the gap. However, the collective drawbacks of the STM setup can be eliminated by incorporating the recognition reagent, optimized for sensitivity, within an electrode tunneling gap in a nanopore channel.

Accordingly, in one embodiment, the sensor includes surface modification by a reagent. In one aspect, the reagent is capable of forming a non-covalent bond with an association site or an attached target molecule. In a particular aspect, the bond is a hydrogen bond. Non-limiting examples of the reagent include 4-mercaptobenzamide and 1-H-Imidazole-2-carboxamide.

Furthermore, the methods of the present technology can provide DNA delivery rate control for one or more recognition tunneling sites, each positioned in one or both of the nanopore channels, and voltage control can ensure that each target molecule resides in each site for a sufficient duration for robust identification.

Sensors in the devices and methods of the present disclosure can comprise gold, platinum, graphene, or carbon, or other suitable materials. In a particular aspect, the sensor includes parts made of graphene. Graphene can act as a conductor and an insulator, thus tunneling currents through the graphene and across the nanopore can sequence the translocating DNA.

In some embodiments, the tunnel gap has a width from about 1 nm to about 20 nm. In one aspect, the width of the gap is at least about 1 nm, or alternatively, at least about 1.5, 2, 2.5, 3, 3.5, 4, 4.5, 5, 6, 7, 8, 9, 10, 12, or 15 nm. In another aspect, the width of the gap is not greater than about 20 nm, or alternatively, not greater than about 19, 18, 17, 16, 15, 14, 13, 12, 11, 10, 9, 8, 7, 6, 5, 4, 3, or 2 nm. In some aspects, the width is between about 1 nm and about 15 nm, between about 1 nm and about 10 nm, between about 2 nm and about 10 nm, between about 2.5 nm and about 10 nm, or between about 2.5 nm and about 5 nm.

In other embodiments, the tunnel gap is suitable for detecting micro-sized particles (eg., viruses, bacteria, and/or cells) and has a width from about 1000 nm to about 100,000 nm. In some embodiments, the width of the gap is between about 10,000 nm and 80,000 nm or between about 20,000 nm and 50,000 nm. In another embodiment, the width of the gap is between about 50,000 nm and 100,000 nm. In some embodiments, the width of the gap is not greater than about 100,000 nm, 90,000 nm, 80,000 nm, 70,000 nm, 60,000 nm, 50,000 nm, 40,000 nm, 30,000 nm, 20,000 nm, 10,000 nm, 9000 nm, 8000 nm, 7000 nm, 6000 nm, 5000 nm, 4000 nm, 3000 nm, 2000 nm, or 1000 nm.

In some embodiments, the sensor is an electric sensor. In some embodiments, the sensor detects a fluorescent detection means when the target molecule or the detectable label passing through has a unique fluorescent signature. A radiation source at the outlet of the pore can be used to detect that signature.

Methods and embodiments for using an auxiliary sensor with the invention described herein are further provided in US Publication No. 2004/0318964, herein incorporated by reference in its entirety.

EXAMPLES

The present technology is further defined by reference to the following example and experiments. It will be apparent to those skilled in the art that many modifications may be practiced without departing from the scope of the current invention The example section begins by first pointing out principal reasons to use a polymer scaffold and fusion molecules in biomarker detection. One reason is that a biomarker alone, below a certain size threshold, is undetectable with a nanopore, as shown for proteins of varying sizes in Calin Plesa, Stefan W. Kowalczyk, Ruben Zinsmeester, Alexander Y. Grosberg, Yitzhak Rabin, and Cees Dekker. "Fast translocation of proteins through solid state nanopores." Nano letters 13, no. 2 (2013): 658-663. Moreover, even those biomarkers that are detectable are generally not distinguishable. In particular, a biomarker will yield the same nanopore signature as all other molecules of comparable size/charge, preventing discrimination. By using a scaffold and fusion molecules, we avoid both of these problems. In particular, we show by examples that detection of representative fusion molecules on scaffolds in a nanopore, and further that detection of target molecules to fusion molecules on the scaffold, can both be detected with a nanopore. With this capability, discrimination can be achieved by appropriate engineering of the ligand domain of the fusion molecule, to achieve specificity for the target molecule of interest.

Example 1

DNA Alone in Solid-state Nanopore Experiment

Figures 6A, 6B, 6C:
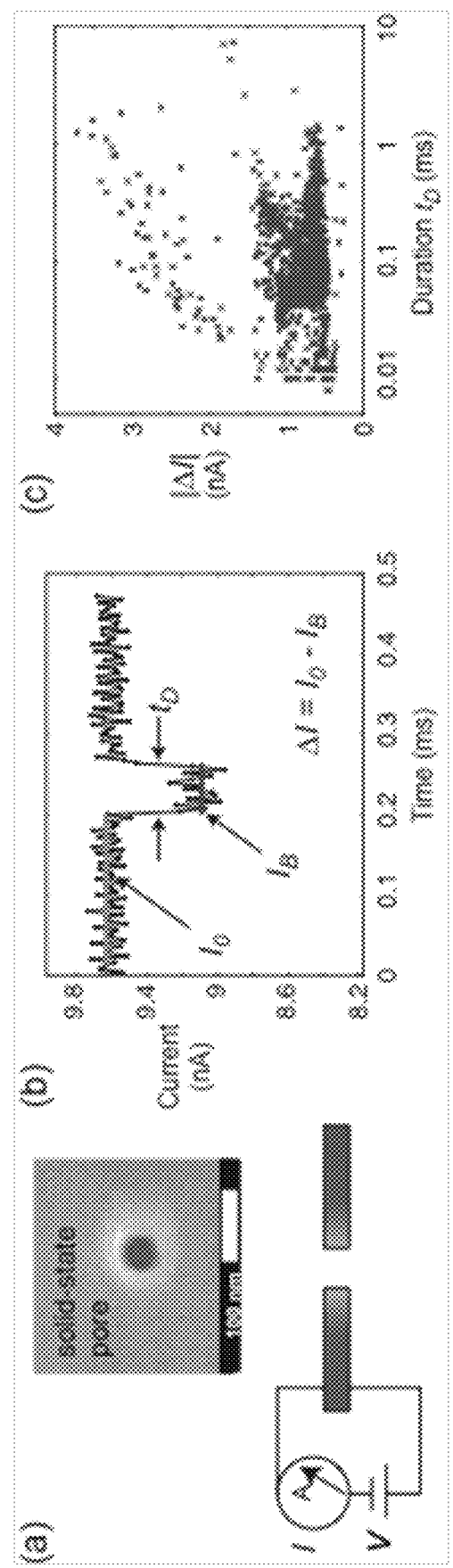
FIGS. 6A, 6B, and 6C illustrate a nanopore device having one pore connecting two chambers and example results from its use. Specifically.

Nanopore instruments use a sensitive voltage-clamp amplifier to apply a voltage V across the pore while measuring the ionic current I0 through the open pore (FIG. 6A). When a single charged molecule such as a double-stranded DNA (dsDNA) is captured and driven through the pore by electrophoresis (FIG. 6B), the measured current shifts from $I_0$ to $I_B$, and the shift amount $\Delta I = I_0 - I_B$ and duration $t_D$ are used to characterize the event. After recording many events during an experiment, distributions of the events (FIG. 6C) are analyzed to characterize the corresponding molecule. In this way, nanopores provide a simple, label-free, purely electrical single-molecule method for biomolecular sensing.

In the DNA experiment shown in FIGS. 6A, 6B, and 6C, the single nanopore fabricated in silicon nitride (SiN) substrate is a 40 nm diameter pore in 100 nm thick SiN membrane (FIG. 6A). In FIG. 6B, the representative current trace shows a blockade event caused by a 5.6 kb dsDNA passing in a single file manner (unfolded) through an 11 nm diameter nanopore in 10 nm thick SiN at 200 mV and 1M KCl. The mean open channel current is I0=9.6 nA, with mean event amplitude IB=9.1 nA, and duration tD=0.064 ms. The amplitude shift is ΔI=I0−IB=0.5 nA. In FIG. 6C, the scatter plot shows |ΔI| vs. tD for all 1301 events recorded over 16 minutes.

Figures 7A, 7B:
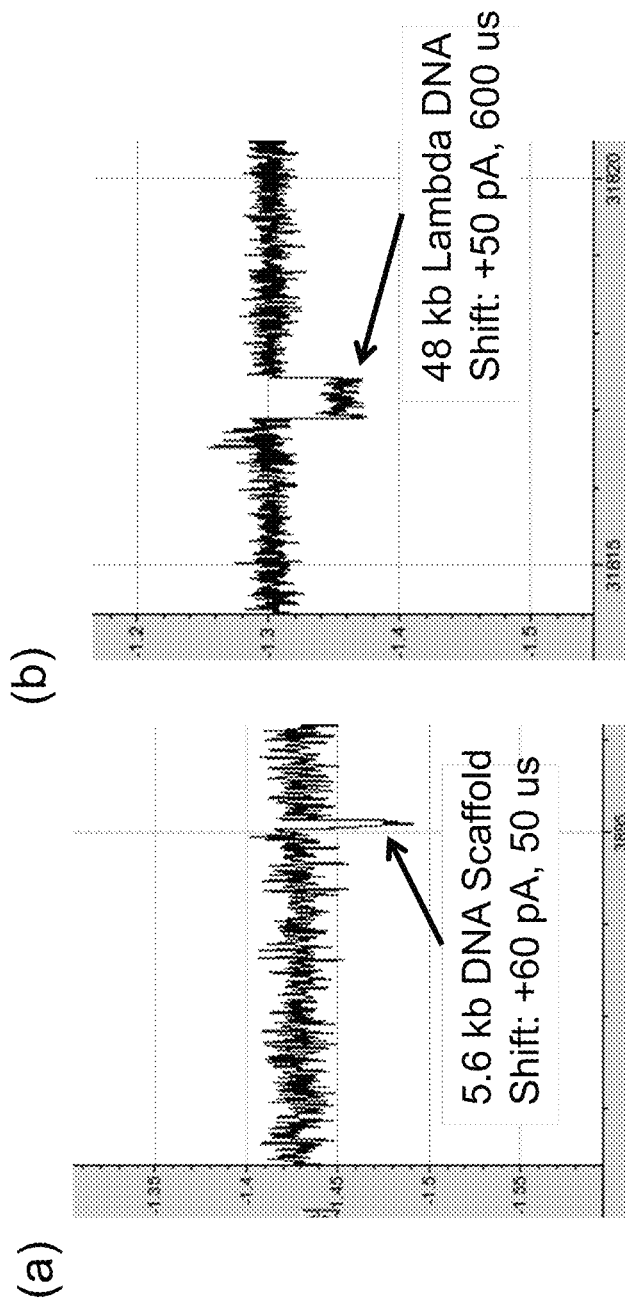
FIGS. 7A and 7B depict current traces measured within one embodiment of a nanopore device fabricated in accordance with the present invention. The provided current traces show that unbound dsDNA causes current enhancement events at KCl concentrations below 0.4 M. Current enhancements appeared as downward shifts in the provided experiment, since the voltage and current are both negative (as in FIG. 3C). Specifically, in DNA alone control experiments using a 10-11 nm diameter pore in 0.1M KCl at −200 mV, 5.6 kb dsDNA scaffold (FIG. 7A) causes brief current enhancement events that are 50-70 pA in amplitude and 10-200 microseconds in duration. Likewise, 48 kb Lambda DNA (FIG. 7B) causes current enhancement events 50-70 pA in amplitude and 50-2000 microseconds in duration.

In the DNA experiment shown in FIGS. 7A and 7B, dsDNA alone causes current enhancement events at 100 mM KCl. This was shown in the published research of Smeets, Ralph M M, et al. "Salt dependence of ion transport and DNA translocation through solid-state nanopores." Nano Letters 6.1 (2006): 89-95. The study showed that, while the amplitude shift ΔI=I0−IB>0 for KCl concentration above 0.4 M, the shift has opposite polarity (ΔI<0) for KCl concentration below 0.4 M. As this is a negative voltage experiment (−200 mV) with KCl concentration below 0.4 M, we see that the DNA event has the same polarity (316) relative to the baseline (315) as shown in FIG. 3C.

Example 2

RecA Protein Binding to DNA Scaffold and Nanopore Detection

This example demonstrates the ability to use the elements of a fusion molecule to detect a target biomarker. The fusion molecule used in this example consists of the portion of RecA that binds DNA (i.e. the DNA binding domain) and the portion of RecA (epitope) that baits the biomarker (anti-RecA antibody). DNA and RecA experiments were performed first in the absence and then in the presence of anti-RecA antibody.

Reagent DNA/RecA consists of the 5.6 kb dsDNA scaffold molecule coated in RecA. RecA is a 38 kDa bacterial protein involved in DNA repair, which is capable of polymerizing along dsDNA (see [C Bell. Structure and mechanism of *Escherichia coli* RecA ATPase. Molecular microbiology, 58(2):358-366, January 2005]). This reagent is created by incubating 60 nM scaffold with 112 uM RecA protein in 10 mM gamma-S-ATP, 70 mM Tris pH 7.6, 10 mM MgCl, and 5 mM DTT (New England Biolabs). Gamma-S-ATP is included since RecA binds to dsDNA with greater affinity if the RecA has ATP bound. Since RecA can hydrolyze ATP to ADP, thereby reducing its affinity for DNA, the non-hydrolyzable gamma-S ATP analog prevents this transition to ADP and thus the higher affinity state is maintained. Even though the ratio of RecA to DNA is one RecA molecule for every possible 3-bp binding site, we expect that not all the RecA protein is binding and thus there is free RecA in solution, as observed in other nanopore studies (see Smeets, R. M. M., S. W. Kowalczyk, A. R. Hall, N. H. Dekker, and C. Dekker. "Translocation of RecA coated double-stranded DNA through solid-state nanopores." Nano letters 9, no. 9 (2008): 3089-3095, and Kowalczyk, Stefan W., Adam R. Hall, and Cees Dekker. "Detection of local protein structures along DNA using solid-state nanopores." Nano letters 10, no. 1 (2009): 324-328). DNA/RecA samples are then adjusted to 1M KCl or LiC1, 10 mM EDTA and tested in a nanopore experiment or excess RecA protein is removed using gel filtration (ThermoScientific Spin Columns).

Figure 8:
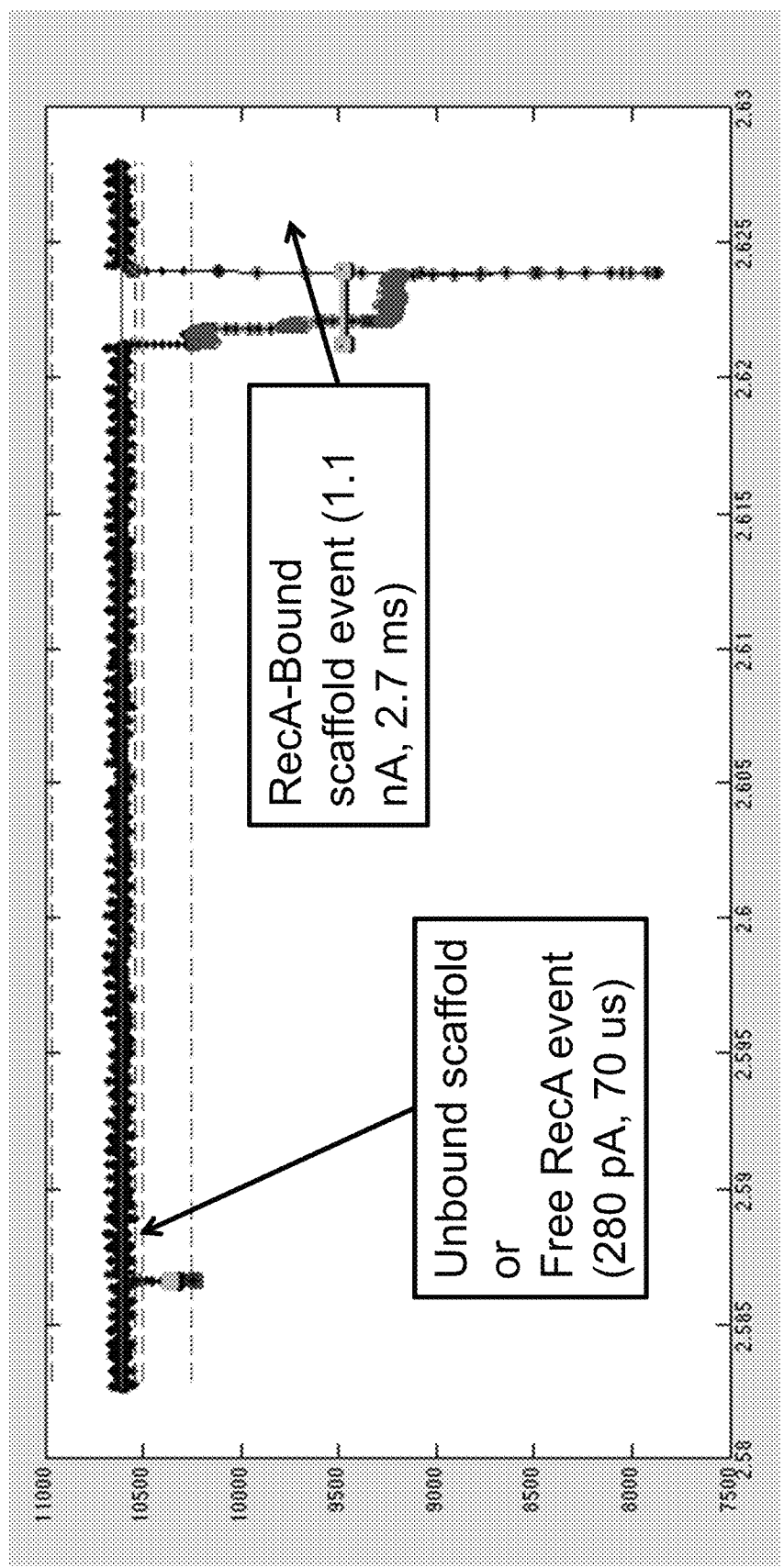
FIG. 8 shows two representative current events depicted in a current profile captured in an experiment with 5.6 kb dsDNA scaffold and RecA protein at 180 mV and 1M KCl using a 16-18 nm diameter nanopore. The first event is consistent with an unbound dsDNA or possibly a free RecA (or multiple associated RecA proteins) passing through the pore, at 280 pA mean current attenuation lasting 70 microseconds. The second event is consistent with RecA-bound scaffold passing through the pore, at 1.1 nA mean current attenuation lasting 2.7 milliseconds. RecA-bound events commonly display deeper blockades with longer duration.
Figure 9:
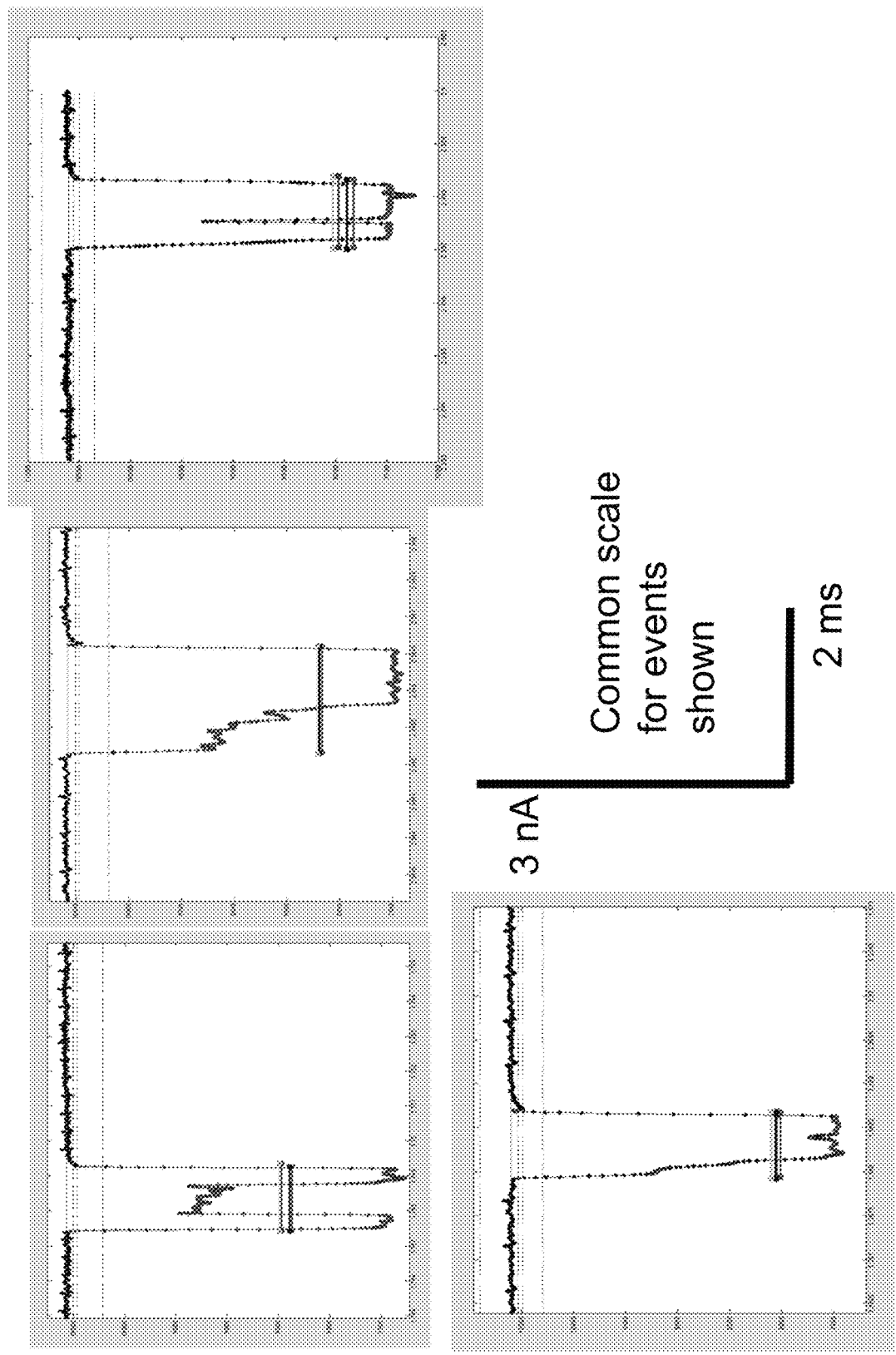
FIG. 9 depicts four more current profiles, each showing a representative current event consistent with RecA-bound scaffold passing through the pore.

In one set of experiments, we used a 16-18 nm diameter pore formed in a 30 nm thick SiN membrane, applying 180 mV in 1M KCl at pH 8. In separate control experiments, unbound 5.6 kb dsDNA scaffold generates 95% of events in the range of 2100-400 pA and 530-500 microseconds. Also, free RecA events are 2100-600 pA, 20-200 usec. Finally, RecA-bound DNA events are typically much deeper blockades, in the range 0.51-3 nA, and with longer duration (0.200-3 milliseconds). Representative events for RecA-bound DNA are shown in FIG. 8 and FIG. 9.

These events have interesting patterns, which in the paper by Kowalczyk et al. ["Detection of local protein structures along DNA using solid-state nanopores." Nano letters 10, no. 1 (2009): 324-328] the authors attempt to infer the location and length of RecA filaments that are bound to each DNA. However, this is speculative, since it assumes a uniform passage rate through the pore even though another study showed that dsDNA does not pass through a pore at a uniform rate [Lu, Bo, et al. "Origins and consequences of velocity fluctuations during DNA passage through a nanopore." Biophysical journal 101.1 (2011): 70-79].

Figure 10A:
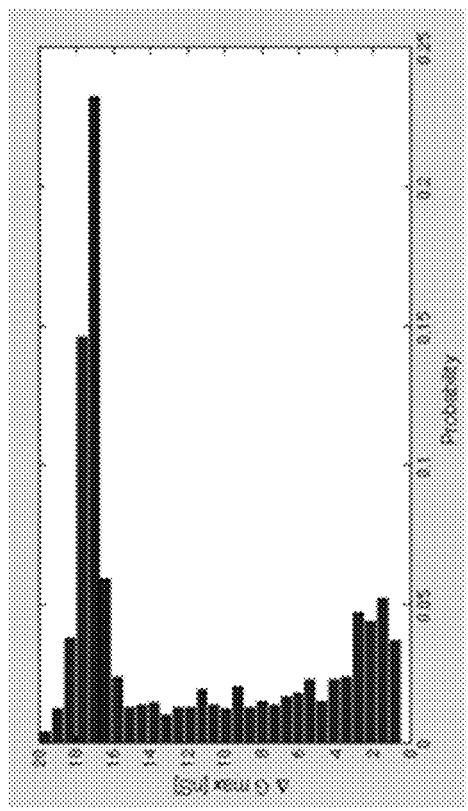
FIGS. 10A, B, C, and D shows scatter plots and histograms depicting all 1385 events during one experiment with RecA and DNA recorded over 10 minutes, using embodiments of methods described herein. In the depicted graphs, one data point is provided for each event. In particular, the depicted graphs show.
Figure 10B:
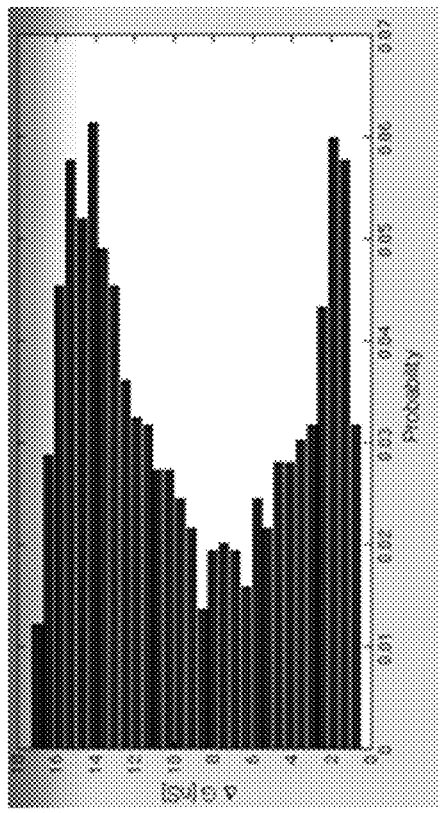
(FIG. 10B) a probability histogram of the maximum conductance shift values.
Figure 10C:
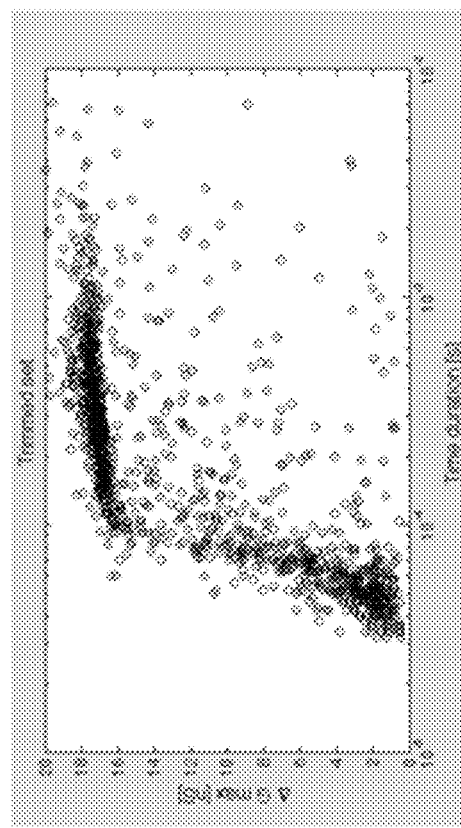
(FIG. 10C) mean conductance (mean current shift divided by voltage) vs. time duration, with time duration on a log-scale.
Figure 10D:
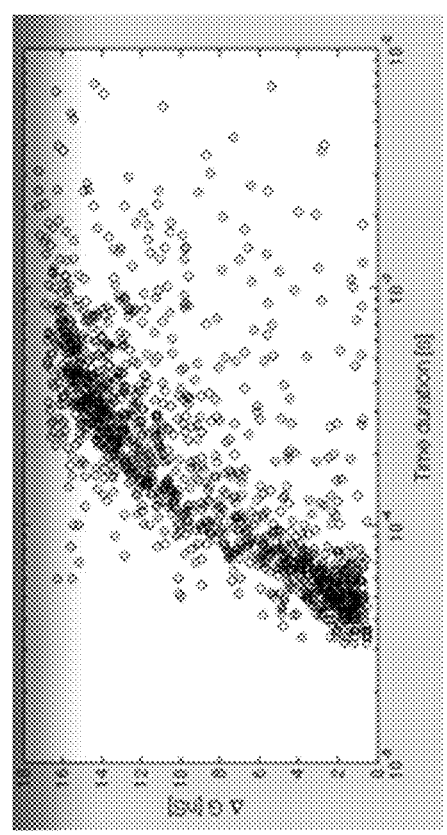
(FIG. 10D) a probability histogram of the mean conductance values. The data sets are the same in (FIGS. 10A and 10B) and (FIGS. 10C and 10D), but showing a different variable for quantifying the conductance shift (maximum in (FIGS. 10A and 10B), mean in (FIGS. 10C and 10D). Both show event populations consistent with free RecA (30-100 microseconds in duration, and below 8 nS in conductance shift) and with RecA-bound DNA (100-10,000 microseconds in duration, and above 8 nS in conductance shift), FIGS. 11A, 11B, and 11C illustrate results from a nanopore device detecting DNA/RecA complexes and RecA-antibody on DNA/RecA complexes, and the results differentiating these complexes from unbound DNA and also from free RecA.

The event scatter plots in FIGS. 10A and 10C show on the vertical axis the maximum and mean current shift, respectively, normalized by voltage (conductance is current normalized by voltage, hence these are the maximum and mean conductance shifts), and the event duration on the horizontal axis. The maximum conductance is denoted "AG max" in FIG. 10A, and the mean is denoted "AG" in FIG. 10C. Both event plots have all 1385 events recorded over 10 minutes. Reporting the event conductance shift values, instead of the current shift values, is common in nanopore research papers. For example, a mean conductance of 14 nS at 200 mV is equivalent to a mean current amplitude of 2.8 nA. Observe that there are two apparent sub-populations in amplitude (or equivalently, conductance) and duration, with the deeper and longer duration events attributable to RecA-bound DNA and the faster shallower events attributable to free RecA in solution. We verified the identity of the faster, shallower subpopulation as free RecA by running RecA alone control experiments. This was also verified in the earlier study [Smeets, R. M. M., S. W. Kowalczyk, A. R. Hall, N. H. Dekker, and C. Dekker. "Translocation of RecA coated double-stranded DNA through solid-state nanopores." Nano letters 9, no. 9 (2008): 3089-3095]. Looking at the maximum current shift value (FIGS. 10A and 10B) instead of the mean (FIGS. 10C and 10D) makes the subpopulations events more distinct (note, each plot from FIGS. 10A, 10B, 10C, and 10D uses the same source data, but reports for each event the maximum conductance shift in (FIGS. 10A and 10B) vs. the mean conductance shift in (FIGS. 10C and 10D)). RecA-bound DNA vs. unbound DNA event patterns are consistent with the model signal patterns in FIG. 3A.

Figure 11C:
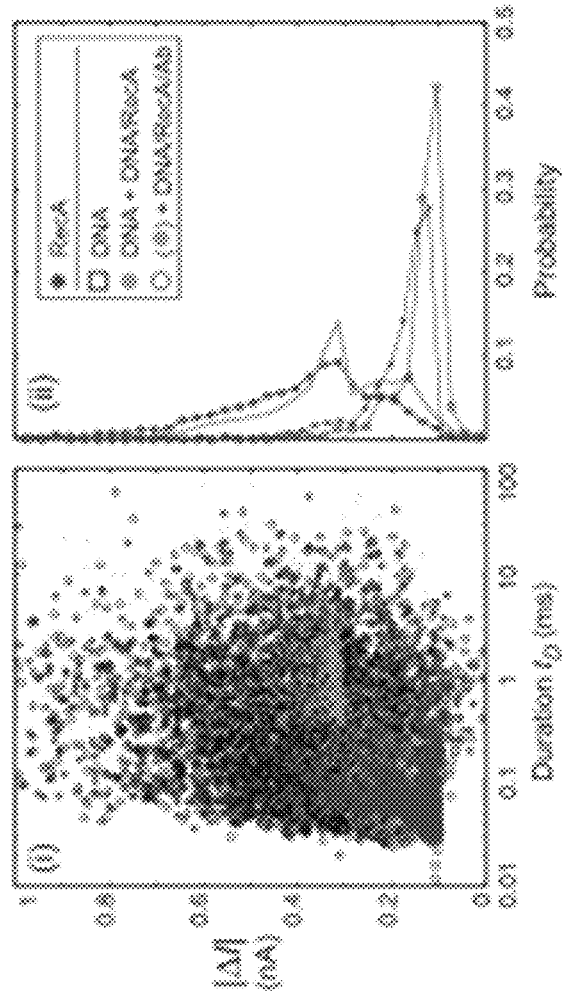
FIG. 11C depicts a (i) Event scatter plot of mean current shift vs. duration ($|\Delta I|$ vs. $t_D$) and (ii) horizontal probability histogram of $|\Delta I|$ for two separate experiments overlaid. In a RecA alone control experiment, 0.5 uM RecA (*) was measured at 180 mV in 1M KCl with a 20 nm diameter pore, generating 767 events over 10 min. Note that only 0.6% of RecA events exceed a criteria of (600 pA, 0.2 ms) under these conditions. In another experiment, three reagents were added in sequence in 1M LiCl. First, 0.1 uM DNA (□) was measured at 200 mV with a 20 nm diameter pore, generating 402 events at 0.1 events/sec. After the pore enlarged to 27 nm, 1.25 nM DNA/RecA (•) was added, generating 3387 events at 1.44 events/sec. Lastly, 1.25 nM DNA/RecA/Ab (○) was added generating 4953 events at 4.49 events/sec. Fraction of events exceeding the [600 pA, 0.2 ms] criteria grew monotonically from 0% with DNA alone, to 5.2% (176) with DNA/RecA added, and up to 9.8% (485) with DNA/RecA/Ab added.
Figure 11A:
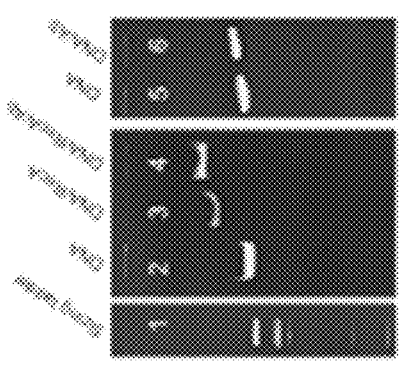
FIG. 11A is a gel shift assay. The DNA/RecA/mAb ARM191 Gel Shift Experiments (EMSA) have lanes: 1) Ladder, top rung 5000 bp; 2) Scaffold DNA only in RecA labeling buffer; 3) DNA/RecA complex, 1:1 RecA protein to RecA binding sites; 4) DNA/RecA/Ab complex, DNA/Rec incubated with a 1:2000 dilution of monoclonal Ab ARM191; 5) Scaffold DNA only in Ab labeling buffer; and 6) Scaffold DNA mixed with mAb (ARM191).

In separate experiments, to demonstrate detection of a target antibody, RecA antibody was used. The DNA/RecA reagent binds an antibody biomarker creating a DNA/RecA/Ab complex by incubating one nanomolar DNA/RecA for 30 mins with either an anti-RecA monoclonal antibody (ARM191, Fisher Scientific) or polyclonal RecA anti-serum (gift from Prof. Ken Knight, Ph. D., UMass Medical School), at a 1:10000 dilution. Electrophoretic mobility shift assays, 5% TBE polyacrylamide gel in 1×TBE buffer, are used to test the DNA/RecA and DNA/RecA/Ab complexes by comparing migration of complexes to DNA only or the proper controls. FIG. 11A shows a clear shift for DNA/RecA/mAb above DNA/RecA, which is in turn well above the unbound 5.6 kb dsDNA scaffold.

Figure 11B:
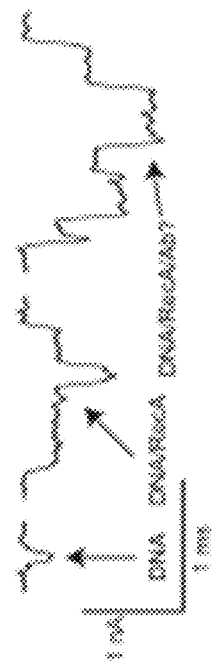
FIG. 11B shows representative events for DNA (230 pA, 0.1 ms), DNA/RecA (390 pA, 1.1 ms), and probable DNA/RecA/Ab (860 pA, 1.5 ms). RecA-bound DNA event amplitudes are uniformly smaller than in earlier figures (FIGS. 8, 9, 10A, 10B, 10C, and 10D) since the pore used to measure these events is considerably larger (27-29 nm in diameter).

This complex was tested experimentally with a nanopore. The nanopore experiments were run at 200 mV in 1M LiCl with a pore that varied in diameter: 20 nm during the DNA alone control, and then enlarged to 27 nm after RecA-bound DNA complexes were added. To run the assay, 0.1 nM DNA was added to the chamber above the pore. After 10 minutes of recording nanopore translocation events at 200 mV, 1.25 nM DNA/RecA was added. After another period of recording nanopore translocation events at 200 mV, 1.25 nM DNA/RecA/mAb was added. With the Ab-bound complexes in solution, a new multi-level event type was observed (FIG. 11B) that did not match event patterns characteristic of the other two complex types (DNA, DNA/RecA). The ΔI vs. tD distributions of events recorded during each phase of the experiment (FIG. 11C) show that RecA-bound DNA events have longer durations tD, and 3 times as many events had a mean amplitude shift ΔI greater than 0.6 nA after DNA/RecA/mAb was added. A simple criteria for tagging events in this data set as also being Ab-bound is (ΔI, tD)>(0.6 nA, 0.2 ms). Thus, we identified a best signature that is almost absent in unbound DNA events, but is present in a significant fraction of RecA-bound events (with or without antibody also bound to DNA/RecA). We used this signature for detection of the presence of RecA-bound DNA complexes in solution above the nanopore. For the purpose of antibody detection, we take this a step further, and identified a best signature that was almost absent in unbound DNA and RecA-bound DNA event types, but was present in a significant fraction of RecA-bound events with antibody also bound to DNA/RecA. This provided a criterion for detection of the presence of RecA-bound DNA complexes in solution above the nanopore. The DNA and RecA and RecA-antibody experiments were done with a positive voltage with KCl concentration above 0.4 M. As shown in FIG. 11B, we have provided a system where the event patterns are comparable to the idealized patterns in FIG. 3A.

The invention claimed is:

1. A method for detecting the presence or absence of a target molecule in a sample, comprising:
    a) contacting the sample with a complex comprising a polymer scaffold bound to a fusion molecule, wherein the fusion molecule comprises a target molecule binding domain for selectively binding to the target molecule, and wherein the fusion molecule is non-specifically bound to the polymer scaffold;
    b) loading the complex into a device comprising a pore that separates an interior space of the device into two volumes to allow the complex to pass through the pore from one volume to the other volume, wherein the device comprises a sensor for identifying objects passing through the pore; and
    c) determining, with the sensor, whether the target molecule binding domain is bound to a target molecule upon translocation of the complex through the pore, thereby detecting the presence or absence of the target molecule in the sample.

2. The method of claim 1, wherein the polymer scaffold comprises a polynucleotide or a polypeptide.

3. The method of claim 2, wherein said polynucleotide comprises a deoxyribonucleic acid (DNA), a ribonucleic acid (RNA), or a peptide nucleic acid (PNA).

4. The method of claim 1, wherein the target molecule is selected from the group consisting of: a protein, a peptide, a polynucleotide, a chemical compound or element, and an ion.

5. The method of claim 1, wherein the determining step is performed $1\times10^3$, $1\times10^4$, $1\times10^5$, $1\times10^6$ or more times for each sample.

6. The method of claim 1, wherein the fusion molecule comprises a polymer scaffold binding domain.

7. The method of claim 6, wherein said polymer scaffold comprises a polynucleotide.

8. The method of claim 7 wherein said polymer scaffold binding domain binds to the backbone of the polynucleotide.

9. The method of claim 7, wherein said polymer scaffold binding domain binds a chemically modified region of said polymer scaffold.

10. The method of claim 9, wherein said chemical modification is selected from the group consisting of: acetylation, methylation, glycosylation, phosphorylation, biotinylation, and oxidation.

11. The method of claim 7, wherein said polymer scaffold binding domain recognizes and binds a sequence of no more than 6, 5, 4, 3, or 2 nucleotides.

12. The method of claim 1, wherein said polymer scaffold comprises a non-engineered binding domain recognized by the polymer scaffold binding domain of the fusion molecule.

13. The method of claim 1, wherein step (a) is performed prior to step (b).

14. The method of claim 1, wherein step (b) is performed prior to step (a).

15. The method of claim 1, wherein the sensor comprises electrodes that apply a voltage differential between the two volumes and measure current flow through the pore.

16. The method of claim 1, wherein the device comprises an upper chamber, a middle chamber and a lower chamber, wherein the upper chamber is in communication with the middle chamber through a first pore, and the middle chamber is in communication with the lower chamber through a second pore;

wherein the first pore and second pore simultaneously translocate the same polymer scaffold; and wherein each of the chambers comprises an electrode for connecting to a power supply.

17. The method of claim 16, further comprising applying independent voltages across each pore with a common ground in the middle chamber to capture the polymer first into both pores, and subsequently using voltage control logic to move and control the polymer scaffold in any direction after the fusion molecule bound to the polymer scaffold passes through the pore, to detect and re-detect whether the fusion molecule bound is bound to a target molecule or particle.

* * * * *